US007771953B2

(12) United States Patent
Ross

(10) Patent No.: US 7,771,953 B2
(45) Date of Patent: Aug. 10, 2010

(54) METHODS OF DIAGNOSING AND TREATING CANCER

(75) Inventor: Jeffrey S. Ross, Lebanon Springs, NY (US)

(73) Assignee: Millenium Pharmaceuticals, Inc., Cambridge, MA (US)

( * ) Notice: Subject to any disclaimer, the term of this patent is extended or adjusted under 35 U.S.C. 154(b) by 722 days.

(21) Appl. No.: 10/736,112

(22) Filed: Dec. 15, 2003

(65) Prior Publication Data

US 2004/0214204 A1 Oct. 28, 2004

Related U.S. Application Data

(60) Provisional application No. 60/439,205, filed on Jan. 10, 2003.

(51) Int. Cl.
*G01N 33/53* (2006.01)

(52) U.S. Cl. ........................ 435/7.1; 435/7.92; 530/350

(58) Field of Classification Search .................. 435/7.1, 435/7.23, 7.92; 530/387.1, 350
See application file for complete search history.

(56) References Cited

U.S. PATENT DOCUMENTS

| | | | |
|---|---|---|---|
| 4,454,106 | A | 6/1984 | Gansow et al. |
| 4,472,509 | A | 9/1984 | Gansow et al. |
| 4,814,275 | A | 3/1989 | Durda et al. |
| 4,855,353 | A | 8/1989 | Kurami et al. |
| 4,863,851 | A | 9/1989 | McEwan et al. |
| 4,863,854 | A | 9/1989 | Mattes et al. |
| 4,885,363 | A | 12/1989 | Tweedle et al. |
| 5,013,645 | A | 5/1991 | Kim |
| 5,053,503 | A | 10/1991 | Dean et al. |
| 5,057,302 | A | 10/1991 | Johnson et al. |
| 5,118,611 | A | 6/1992 | Smith et al. |
| 5,130,118 | A | 7/1992 | Johnson et al. |
| 5,162,504 | A | 11/1992 | Horoszewicz |
| 5,198,208 | A | 3/1993 | Berg et al. |
| 5,208,324 | A | 5/1993 | Klaveness et al. |
| 5,217,704 | A | 6/1993 | Johnson et al. |
| 5,227,471 | A | 7/1993 | Wright, Jr. |
| 5,229,289 | A | 7/1993 | Kjeldsen et al. |
| 5,314,996 | A | 5/1994 | Wright, Jr. |
| 5,342,924 | A | 8/1994 | Chang |
| 5,419,893 | A | 5/1995 | Berg et al. |
| 5,474,756 | A | 12/1995 | Tweedle et al. |
| 5,489,525 | A | 2/1996 | Pastan |
| 5,531,978 | A | 7/1996 | Berg et al. |
| 5,538,866 | A | 7/1996 | Israeli et al. |
| 5,565,562 | A | 10/1996 | Parker et al. |
| 5,578,484 | A | 11/1996 | Horoszewicz |
| 5,599,677 | A | 2/1997 | Dowell et al. |
| 5,639,879 | A | 6/1997 | Mease et al. |
| 5,660,827 | A | 8/1997 | Thorpe et al. |
| 5,674,470 | A | 10/1997 | Tweedle et al. |
| 5,697,902 | A | 12/1997 | Goldenberg |
| 5,763,202 | A | 6/1998 | Horoszewicz |
| 5,776,427 | A | 7/1998 | Thorpe et al. |
| 5,804,602 | A | 9/1998 | Slusher et al. |
| 5,846,519 | A | 12/1998 | Tweedle et al. |
| 5,855,866 | A | 1/1999 | Thorpe et al. |
| 5,863,538 | A | 1/1999 | Thorpe et al. |
| 5,877,289 | A | 3/1999 | Thorpe et al. |
| 5,935,818 | A | 8/1999 | Israeli et al. |
| 5,958,474 | A | 9/1999 | Lee et al. |
| 5,965,132 | A | 10/1999 | Thorpe et al. |
| 6,004,554 | A | 12/1999 | Thorpe et al. |
| 6,004,555 | A | 12/1999 | Thorpe et al. |
| 6,022,524 | A | 2/2000 | Maisano et al. |
| 6,036,955 | A | 3/2000 | Thorpe et al. |
| 6,051,230 | A | 4/2000 | Thorpe et al. |
| 6,093,399 | A | 7/2000 | Thorpe et al. |
| 6,107,090 | A | 8/2000 | Bander |
| 6,136,311 | A | 10/2000 | Bander |
| 6,143,274 | A | 11/2000 | Tweedle et al. |
| 6,150,508 | A | 11/2000 | Murphy et al. |
| 6,261,535 | B1 | 7/2001 | Thorpe et al. |
| 6,331,175 | B1 | 12/2001 | Goldenberg |
| 6,649,163 | B1 | 11/2003 | Bander |

FOREIGN PATENT DOCUMENTS

| | | | |
|---|---|---|---|
| EA | 4634 | B1 | 6/2004 |
| EP | 0 208 531 | B1 | 1/1987 |
| EP | 0 232 751 | B1 | 8/1987 |
| EP | 0 233 619 | B1 | 8/1987 |
| EP | 0 279 397 | B1 | 8/1988 |
| EP | 0 292 689 | B1 | 11/1988 |
| EP | 0 299 795 | A1 | 1/1989 |
| EP | 0 315 188 | B1 | 5/1989 |
| EP | 0 382 583 | B1 | 8/1990 |
| EP | 0 392 423 | A2 | 10/1990 |

(Continued)

OTHER PUBLICATIONS

Oesterreich, S et al, 1996 (Clin Cancer Res, 2: 1199-1206.*
Tockman et al (Cancer Res., 1992, 52:2711s-2718s).*
Vandesompele J et al, 2003 (Oncogene, 22(3): 456-60).*
Schmid S et al, 2001 (J comparative Neurology, 430(2): 160-71).*
Conner et al, 1996 (Mol Brain Res, 42: 1-17).*
Bostwick et al, 1998 (Cancer, 82(11): 2256-2261).*
Beckett et al, 1999 (Clin Cancer Res, 5 (12): 4034-40).*
Rosenthal S A et al, 2001 (Techniques in Urology, 7(1): 27-37).*
Murphy et al, 1998 (Urology, 51: 89-97).*
Thomas et al, 2002 (J Clin Oncology, 20(15): 3213-8).*
ATCC Deposit #HB9131 from Jun. 24, 1986 (Not Available).
Barren et al. .(1997), "Monoclonal Antibody 7E11.C5 Staining of Viable LNCaP Cells", Prostate 30(1):65-68.

(Continued)

*Primary Examiner*—Larry R. Helms
*Assistant Examiner*—Minh-Tam Davis
(74) *Attorney, Agent, or Firm*—Lando & Anastasi, LLP

(57) ABSTRACT

The invention features methods of evaluating the risk of cancer recurrence in a subject diagnosed with cancer.

10 Claims, 7 Drawing Sheets

FOREIGN PATENT DOCUMENTS

| | | | |
|---|---|---|---|
| EP | 0 466 200 | A1 | 1/1992 |
| EP | 0 594 739 | B1 | 5/1994 |
| EP | 0 882 454 | A2 | 12/1998 |
| NZ | 333683 | | 1/2002 |
| WO | WO 86/06384 | | 11/1986 |
| WO | WO 88/02635 | | 4/1988 |
| WO | WO 89/00557 | | 1/1989 |
| WO | WO 89/06979 | | 8/1989 |
| WO | WO 91/15466 | | 10/1991 |
| WO | WO 93/17715 | | 9/1993 |
| WO | WO 93/19668 | | 10/1993 |
| WO | WO 94/04702 | | 3/1994 |
| WO | WO 94/09820 | | 5/1994 |
| WO | WO 94/26297 | | 11/1994 |
| WO | WO 95/26206 | | 10/1995 |
| WO | WO 95/31444 | | 11/1995 |
| WO | WO 96/26272 | | 8/1996 |
| WO | WO 96/39185 | | 12/1996 |
| WO | WO 96/40245 | | 12/1996 |
| WO | WO 97/32862 | | 9/1997 |
| WO | WO 97/35616 | | 10/1997 |
| WO | WO98/03873 | | 1/1998 |
| WO | WO 99/43710 | | 9/1999 |
| WO | WO 00/50457 | | 8/2000 |
| WO | WO 00/52473 | | 9/2000 |
| WO | WO 00/74729 | | 12/2000 |
| WO | WO 02/098885 | | 12/2002 |

OTHER PUBLICATIONS

Carter et al. (1996), "Prostate-specific Membrane Antigen is a Hydrolase with Substrate and Pharmacologic Characteristics of a Neuropeptidase", Proc. Natl. Acad. Sci. U.S.A. 93:749-753.

Chang et al. (1999), "Five Different Anti-Prostate-specific Membrane Antigen (PSMA) Antibodies Confirm PSMA Expression in Tumor-associated Neovasculature", Cancer Research, 59(13):3192-3198.

Diamond et al. (1997), "Monoclonal Antibody 225 Blockade of Prostate Specific Membrane Antigen (PSM) Expression: Potential Novel Therapy for Prostate Cancer", Journal of Urology 157(4 suppl):226 (Abstract 884).

Dillman et al. (1988), "Toxicities Associated with Monoclonal Antibody Infusions in Cancer Patients", Mol. Biother. 1(2):81-85.

Dillman et al. (1994), "Human Anti-Mouse Antibody Response in Cancer Patients Following Single Low-Dose Injections of Radiolabeled Murine Monoclonal Antibodies", Cancer Biotherapy 9(1):17-28.

Fair et al. (1997), "Prostate Specific Membrane Antigen", Prostate 32(2):140-148.

Harlow and Lane (1988), "Antibodies: A laboratory manual", Cold Spring Harbor Laboratory, p. 139-243.

Heston (1997), "Characterization and Glutamyl Preferring Carboxypeptidase Function of Prostate Specific Membrane Antigen: A Novel Folate Hydrolase", Urology 49(3A):104-112.

Horoszewicz et al. (1987), "Monoclonal Antibodies to a New Antigenic Marker in Epithelial Prostatic Cells and Serum of Prostatic Cancer Patients", Anticancer Research 7(5B):927-936.

Israeli et al. (1993), "Molecular Cloning of a Complementary DNA Encoding a Prostate-Specific Membrane Antigen", Cancer Research 53(2):227-230.

Israeli et al. (1994), "Expression of the Prostate-Specific Membrane Antigen", Cancer Research 54(7):1807-1811.

Israeli et al. (1997), "Prostate Specific Membrane Antigen and Other Prostatic Tumor Markers on the Horizon", Urological Clinics of North America 24(2):439-450.

Jain, R.K. (1990), "Vacular and interstitial barriers to delivery of therapeutic agents in tumors", Cancer and Metastasis Reviews 9(3):253-266.

Leek et al. (1995), "Prostate-Specific Membrane Antigen: Evidence for the Existence of a Second Related Human Gene", British Journal of Cancer 72:583-588.

Leung et al. (1986), "Selection of a Monoclonal Antibody to a New Prostate Cancer Marker for In Vivo Clinical Trials", $6^{th}$ International Congress of Immunology, p. 516 (Abstract 4.15.19).

Liu et al. (1997), "Monoclonal Antibodies to the Extracellular Domain of Prostate-specific Membrane Antigen also React with Tumor Vascular Endothelium", Cancer Research 57(18):3629-3634.

Liu, et al. (1998), "Constitutive and Antibody-Induced Internalization of Prostate-Specific Membrane Antigen", Cancer Research 58(18):4055-4060.

Murphy et al. (1995), "Comparison of Prostate Specific Antigen, Prostate Specific Membrane Antigen, and LNCaP-Based Enzyme-Linked Immunosorbent Assays in Prostatic Cancer Patients and Patients With Benign Prostatic Enlargement", The Prostate 26:164-168.

Murphy et al. (1995), "Comparison of Prostate Specific Membrane Antigen, and Prostate Specific Antigen Levels in Prostatic Cancer Patients", Anticancer Res. 15:1473-1480.

Murphy et al. (1996), "Measurement of Prostate-Specific Membrane Antigen in the Serum With a New Antibody", The Prostate 28(4):266-271.

Pinto et al. (1996), "Prostate-Specific Membrane Antigen: A Novel Folate Hydrolase in Human Prostatic Carcinoma Cells", Clincal Cancer Research 2(9):1445-1451.

Rochon et al. (1994), "Western Blot Assay for Prostate-Specific Membrane Antigen in Serum of Prostate Cancer Patients", The Prostate 25(4):219-223.

Schlom (1991), "Monoclonal antibodies: They're more and less than you think", Molecular Foundations of Oncology, ed. Broder, Williams & Wilkins, p. 95-134.

Silver et al. (1997), "Prostate-specific Membrane Antigen Expression in Normal and Malignant Human Tissues", Clinical Cancer Research 3:81-85.

Su et al. (1995), "Alternatively Spliced Variants of Prostate-specific Membrane Antigen RNA: Ratio of Expression as a Potential Measurement of Progression", Cancer Research 55:1441-1443.

Troyer et al. (1994), "Subcellular Localization of the 7E11-C5 Prostate Specific Antigen", Proc. Am. Assoc. Cancer Research 35:283 (Abstract 1688).

Troyer et al. (1995), "Biochemical Characterization and Mapping of the 7E11-C5.3 Epitope of the Prostate-Specific Membrane Antigen", Urol Oncol 1:29-37.

Troyer et al. (1995), "Detection and Characterization of the Prostate-Specific Membrane Antigen (PSMA) in Tissue Extracts and Body Fluids", International Journal of Cancer 62(5):552-558.

Troyer et al. (1997), "Location of prostate-specific membrane antigen in the LNCaP prostate carcinoma cell line", Prostate 30(4):232-242.3

Uria et al. (1997), "Prostate Specific Membrane Antigen in Breast Carcinoma", The Lancet 349(9065):1601.

Wang et al. (1988), "Monoclonal Antibody Assays for Prostatic Tumor", Immunol Ser 39:195-219.

Wright (1990), "Characterization of a New Prostate Carcinoma-Associated Marker: 7E11-C5", Antibody Immunoconjugates and RadioPharmaceuticals 3:Abstract 193.

Wright et al. (1995), "Expression of Prostate-Specific Membrane Antigen in Normal, Benign, and Malignant Prostate Tissues", Urol Oncol, 1:18-28.

Yang et al. (1998), "Alpha particle emitter therapy of micrometastases: $^{213}$Bi-J5 (anti-PSMA) treatment of LNCaP spheroids", Proceedings of the American Association for Cancer Research 39:440 (Abstract #2996).

Adsan et al., "Can the reverse transcriptase-polymerase chain reaction for prostate specific antigen and prostate specific membrane antigen improve staging and predict biochemical recurrence?", BJU International, 90:579-585 (2002).

Loric et al., "Abnormal E-cadherin expression and prostate cell blood dissemination as markers of biological recurrence in cancer", European Journal of Cancer, 37:1475-1481 (2001).

Copy of EP Search Report dated Feb. 22, 2007.

Okegawa et al. "Value of Reverse Transcription Polymerase Chain Reaction Assay in Pathological Stage T3N0 Prostate Cancer", *The Prostate*, vol. 44, No. 3: pp. 210-218 (2000).

Chang et al. The clinical role of prostate-specific membrane antigen (PSMA), *Urologic Oncology*, vol. 7, No. 1: pp. 7-12 (2002).

Okegawa et al., Detection of Micrometastatic Prostate Cancer Cells in the Lymph Nodes by Reverse Transcriptase Polymerase Chain Reaction is Predictive of Biochemical Recurrence in Pathological Stage T2 Prostate Cancer, *The Journal of Urology*, vol. 163, No. 4: pp. 1183-1188 (2000).

* cited by examiner

METHODS OF DIAGNOSING AND TREATING CANCER

CLAIM OF PRIORITY

This application claims priority under 35 USC §119(e) to U.S. Provisional Patent Application Ser. No. 60/439,205, filed on Jan. 10, 2003, the entire contents of which is hereby incorporated by reference.

BACKGROUND OF THE INVENTION

A wide variety of morphology-driven and molecular markers have been studied for their ability to predict disease outcome in prostate cancer. Isaacs et al. (1997) *Am. J. Pathol.* 150:1511-1521; Koch et al. (2000) *J. Urol.* 164:749-753; Alers et al. (2000) *Lab. Invest.* 80:931-942. Traditional morphology driven measures have included tumor grade, volume and pathologic stage. Numerous molecular markers have been proposed for their potential clinical utility including the determination of p21, p27, cyclin D1, p53, bcl-2, E-cadherin, HER-2/neu, matrix metalloproteases, telomerase, GST-π. Isaacs et al. (1997) supra; Koch et al. (2000) supra; Alers et al. (2000) supra; Ross et al. (2002) *Exp. Rev. Mol. Diagn.* 2:129-142; Stattin et al. (1997) *Scand J Urol Nephrol Suppl.* 185:1-46. Expanded use of these markers for the individualization of therapy, however, has been hampered by several factors including a lack of universal acceptance of their prognostic significance, problems concerning the specificity and sensitivity of the available testing platforms for each marker, and limited available tissue.

Prostate specific membrane antigen (PSMA) is transmembrane folate hydrolase consisting of 750 amino acids and having a molecular weight of 110 kDa. Israeli et al. (1994) *Cancer Res.* 54:1807-1811; Murphy et al. (1998) *J. Urol.* 160:2396-2401; Tasch et al. (2001) *Crit. Rev. Immunol* 21:249-261. PSMA expression has been consistently demonstrated by immunohistochemistry (IHC) and other techniques in normal and hyperplastic prostate tissues, in prostatic intraepithelial neoplasia (PIN) and in invasive carcinomas. Silver et al. (1997) *Clin Cancer Res.* 3:81-85; Murphy et al. (1998) *Cancer* 83:2259-2269; and Bostwick et al. (1998) *Cancer* 82:2256-2261. PSMA expression and PSMA enzymatic activity are greater in prostate cancer specimens than in benign prostate tissues. Bostwick et al (1998) supra; Lapidus et al. (2000) *Prostate* 45:350-354. The finding that PSMA is expressed in metastatic prostate cancer has lead to the initial development of diagnostic imaging strategies using anti-PSMA antibodies and subsequently to clinical testing of radio-conjugated anti-PSMA antibodies for the treatment of metastatic disease. Gong et al. (1999) *Cancer Metast Rev.* 18:483-490; Gong et al. (2000) *Mol Urol.* 4:217-222; Holmes (2001) *Expert Opin Investig Drugs* 10:5111-519. The identification of PSMA expression in the neo-vasculature of non-prostate cancers has also encouraged the potential use of anti-PSMA antibody therapies for patients with carcinomas of the kidney, lung, colon, breast and other organs. Liu et al. (1997) *Clin Cancer Res* 5:2674-2681; Chang et al. (1999) *Cancer Res.* 59:3192-3198.

SUMMARY OF THE INVENTION

The invention is based, in part, on the discovery that a subset of subjects having prostate cancer over-express PSMA as compared to PSMA levels in other patients having prostate cancer, and that over-expression of PSMA in this subset can be used to predict disease recurrence. According to the American Cancer Society, nearly 40% of men with prostate cancer have local recurrence of the disease after surgery, and approximately 11% are at high risk for metastatic spread of the disease. It has been found that PSMA over-expression in subjects having prostate cancer can be used to determine the likelihood of cancer recurrence in the subject independent of other factors such as Gleason grade and/or cancer stage.

Accordingly, in one aspect, the invention features a method of determining if a subject is at risk for cancer recurrence, e.g., prostate cancer recurrence. The method includes: providing a subject, e.g., a subject diagnosed with a cancer, e.g., prostate cancer; and determining PSMA expression levels in the subject, wherein increased PSMA expression levels, e.g., as compared to a reference standard, e.g., levels of a control subject diagnosed with the cancer, are indicative of a risk of cancer recurrence, to thereby determine if the subject is at risk of cancer recurrence.

In one embodiment, the method includes providing a sample from the subject, and determining PSMA expression levels in the sample. The sample can be a biological sample, e.g., a fluid sample (e.g., serum, semen or urine), or a tissue sample, e.g., a tissue from a prostatic or cancerous lesion (e.g., a biopsy sample or a sample obtained from a lesion removed from the subject, e.g., a primary or metastatic lesion). In one embodiment, the subject has prostate cancer and the sample is obtained from a partial or radical prostatectomy of the subject. In another embodiment, the sample is obtained from a biopsy sample. Thus, in some embodiments, the risk of recurrence can be evaluated upon diagnoses of a subject with cancer, e.g., from the biopsy sample, or can be made after diagnoses, e.g., after a subject has been given an anti-cancer treatment, e.g., after a partial or radical prostatectomy. In yet another embodiment, PSMA expression levels can be determined from a fluid sample, e.g., a blood or urine sample. The sample can be obtained before treatment with an anti-cancer therapy, concurrently with treatment, and/or post treatment.

In some embodiments, PSMA protein amounts can be determined using any suitable assay, such as by using an anti-PSMA antibody, e.g., in an enzyme linked immunosorbant assay (ELISA), a radioimmunoassay (RIA), a Western blot or an immunohistochemical method. Alternatively, the level of PSMA expression can be determined by the amount of PSMA nucleic acid (e.g., mRNA) in the biological sample. For example, PSMA nucleic acids expression (e.g., mRNA levels) amounts can be readily determined using any suitable assay, such as Northern blotting, RT-PCR, or the use of biochips.

In some embodiments, the risk of recurrence in a subject having increased PSMA expression levels is greater than 50%, 60%, 65%, 70%, 75%, 80% or more.

In one embodiment, the method further includes selecting a treatment, e.g., an anti-cancer therapy, for the subject based upon the risk of recurrence. In one embodiment, the PSMA levels in the subject are not increased (i.e., are not increased by a statistically significant amount) as compared to the reference control and the treatment selected is one or more of: surgery (e.g., a partial or radical prostatectomy), cryotherapy and radiation therapy.

In another embodiment, the method further includes selecting a treatment for a subject, when the subject's PSMA levels are increased as compared to the reference control. The treatment selected can be, e.g., one or more of: surgery (e.g., partial or radical prostatectomy); radiation therapy (e.g., external-beam therapy; interstitial-radiation therapy; and a combination of external-beam therapy and interstitial-radiation therapy); chemotherapy; antibody therapy, e.g., administration of a labeled and/or an unlabeled antibody (e.g., administration of an anti-PSMA antibody, e.g., an anti PSMA antibody that binds the extracellular domain of PSMA); and hormonal therapy, which can be administered alone or can be administered before or following radical prostatectomy or radiation (e.g., treatments that reduce serum testosterone concentrations, or inhibit testosterone activity, e.g., administering a leuteinizing hormone-releasing hormone (LHRH) analog or agonist (e.g., Lupron, Zoladex, leuprolide, buserelin, or goserelin) or antagonists (e.g., Abarelix). Non-steroidal anti-androgens, e.g., flutamide, bicalutimade, or nilutamide, can also be used in hormonal therapy, as well as steroidal anti-androgens (e.g., cyproterone acetate or megastrol acetate), estrogens (e.g., diethylstilbestrol), PROSCAR™, secondary or tertiary hormonal manipulations (e.g., involving corticosteroids (e.g., hydrocortisone, prednisone, or dexamethasone), ketoconazole, and/or aminogluthethimide), inhibitors of 5a-reductase (e.g., finisteride), herbal preparations (e.g., PC-SPES), hypophysectomy, and adrenalectomy. Furthermore, hormonal therapy can be performed intermittently or using combinations of any of the above treatments, e.g., combined use of leuprolide and flutamide.

In some embodiments, when the subject's PSMA levels are increased as compared to the reference control, two or more treatments for the subject are selected. For example, the treatments selected can be: surgery (e.g., a partial or radical prostatectomy), cryotherapy and/or radiation and one or more of: chemotherapy; antibody therapy (e.g., administration of a labeled and/or an unlabeled antibody, e.g., administration of an anti-PSMA antibody, e.g., an anti PSMA antibody that binds the extracellular domain of PSMA) and hormonal therapy.

In some embodiments, when the subject has prostate cancer and the subject's PSMA levels are increased as compared to the reference control, the treatment is a prostatectomy (e.g., a partial or radical prostatectomy) and one or more of: chemotherapy, radiation therapy, hormone therapy, antibody therapy (e.g., administration of an anti-PSMA antibody, e.g., an anti PSMA antibody that binds the extracellular domain of PSMA). In preferred embodiments, when the subject has prostate cancer and the subject's PSMA levels are increased as compared to the reference control, the treatment includes a prostatectomy (e.g., a radical or partial prostatectomy) and antibody therapy (e.g., with an antibody that binds the extracellular domain of PSMA, e.g., a labeled or unlabeled antibody that binds the extracellular domain of PSMA).

In some embodiments, the method further includes providing a result of the determination to a third party, e.g., a hospital, clinic, government entity, reimbursing party or insurance company. In other embodiments, payment for a medical procedure, e.g., a treatment, or payment by a reimbursing party, e.g., a government entity or insurance company, is conditional on a selected outcome of the determination method and/or a selected treatment chosen based upon the determination.

In some embodiments, the method further includes evaluating risk of recurrence by a second method, e.g., by assessing the Gleason grade of the cancer and/or assessing the stage of the cancer.

In another aspect, the invention features a method of evaluating a risk of cancer recurrence, e.g., prostate cancer recurrence. The method includes: providing a subject, e.g., a subject diagnosed with cancer, e.g., prostate cancer; detecting the level of PSMA expression, wherein a higher expression level of PSMA is correlated with a risk of cancer recurrence, e.g., prostate cancer recurrence; and assigning a value for the risk of recurrence to the subject.

In some embodiments, a subject having a higher expression level is assigned a value of 50%, 60%, 70%, 80% or more risk of recurrence. In other embodiments, a subject that does not have a higher level of expression is assigned a value of 40%, 35%, 30%, 25%, 20%, 15%, 10% or less of risk of recurrence.

In one embodiment, the method includes providing a sample from the subject, and determining PSMA expression levels in the sample. The sample can be a biological sample, e.g., a fluid sample (e.g., serum, semen or urine), or a tissue sample, e.g., a tissue from a prostatic or cancerous lesion (e.g., a biopsy sample or a sample obtained from a lesion removed from the subject, e.g., a primary or metastatic lesion). In one embodiment, the subject has prostate cancer and the sample is obtained from a partial or radial prostatectomy from the subject. In another embodiment, the sample is obtained from a biopsy sample. Thus, in some embodiments, the risk of recurrence can be evaluated upon diagnoses of a subject with cancer, e.g., from the biopsy sample, or can be made after diagnoses, e.g., after a subject being given an anti-cancer treatment, e.g., after a partial or radical prostatectomy. In yet another embodiment, PSMA expression levels can be determined from a fluid sample, e.g., a blood or urine sample.

In some embodiments, PSMA protein amounts can be determined using any suitable assay, such as by using an anti-PSMA antibody, e.g., in an enzyme linked immunosorbant assay (ELISA), a radioimmunoassay (RIA), a Western blot or an immunohistochemical method. Alternatively, the level of PSMA expression can be determined by the amount of PSMA nucleic acid (e.g., mRNA) in the biological sample. For example, PSMA nucleic acids expression (e.g., mRNA levels) amounts can be readily determined using any suitable assay, such as Northern blotting, RT-PCR, or the use of biochips.

In one embodiment, the method further includes selecting a treatment for the subject based upon the value assigned to the subject for risk of recurrence. In one embodiment, the value assigned to the subject for risk of recurrence is low, e.g., less than 50%, more preferably less than 40%, 30%, and the treatment selected is one or more of: surgery (e.g., a partial or radical prostatectomy), cryotherapy or radiation therapy.

In another embodiment, the method further includes selecting a treatment for a subject where the value assigned to the subject for risk of recurrence is high, e.g., greater than 50%, more preferably greater than 60%, 70%. The treatment selected can be, e.g., one or more of: surgery (e.g., partial or radical prostatectomy); radiation therapy (e.g., external-beam; interstitial-radiation therapy; and a combination of external-beam therapy and interstitial-radiation therapy); chemotherapy; antibody therapy (e.g., administration of a labeled and/or an unlabeled antibody, e.g., administration of an anti-PSMA antibody, e.g., an anti PSMA antibody that binds the extracellular domain of PSMA); hormonal therapy, which can be administered alone or can be administered before or following radical prostatectomy or radiation (e.g., treatments that reduce serum testosterone concentrations, or inhibit testosterone activity, e.g., administering a leuteinizing hormone-releasing hormone (LHRH) analog or agonist (e.g., Lupron, Zoladex, leuprolide, buserelin, or goserelin) or antagonists (e.g., Abarelix). Non-steroidal anti-androgens, e.g., flutamide, bicalutimade, or nilutamide, can also be used in hormonal therapy, as well as steroidal anti-androgens (e.g., cyproterone acetate or megastrol acetate), estrogens (e.g., diethylstilbestrol), PROSCAR™, secondary or tertiary hormonal manipulations (e.g., involving corticosteroids (e.g., hydrocortisone, prednisone, or dexamethasone), ketoconazole, and/or aminogluthethimide), inhibitors of 5a-reductase (e.g., finisteride), herbal preparations (e.g., PC-SPES), hypophysectomy, and adrenalectomy. Furthermore, hormonal therapy can be performed intermittently or using combinations of any of the above treatments, e.g., combined use of leuprolide and flutamide.

In some embodiments, when the value assigned to the subject for risk of recurrence is high, two or more treatments for the subject are selected. For example, the treatments selected can be two or more of: surgery (e.g., a partial or radical prostatectomy), cryotherapy and/or radiation and one or more of: chemotherapy; antibody therapy (e.g., administration of a labeled and/or an unlabeled antibody, e.g., administration of an anti-PSMA antibody, e.g., an anti PSMA antibody that binds the extracellular domain of PSMA) and hormonal therapy.

In some embodiments, when the subject has prostate cancer and the value assigned to the subject for risk of recurrence is high, the treatment is a prostatectomy (e.g., a partial or radical prostatectomy) and one or more of: chemotherapy, radiation therapy, hormone therapy, antibody therapy (e.g., administration of an anti-PSMA antibody, e.g., an anti PSMA antibody that binds the extracellular domain of PSMA). In preferred embodiments, when the subject has prostate cancer and the value assigned to the subject for risk of recurrence is high, the treatment includes a prostatectomy (e.g., a radical or partial prostatectomy) and antibody therapy (e.g., with an antibody that binds the extracellular domain of PSMA, e.g., a labeled or unlabeled antibody that binds the extracellular domain of PSMA).

In some embodiments, the method further includes providing a result of the evaluation, e.g., the assigned value, to a third party, e.g., a hospital, clinic, government entity, reimbursing party or insurance company. In other embodiments, payment for a medical procedure, e.g., a treatment, or payment by a reimbursing party, e.g., a government entity or insurance company, is conditional on a selected outcome, e.g., the assigned value, of the evaluation method and/or the treatment selected based upon the assigned value.

In some embodiments, the method further includes evaluating risk of recurrence by a second method, e.g., by assessing the Gleason grade of the cancer and/or assessing the stage of the cancer. In some embodiments, the method further includes modifying the value assigned for risk of recurrence such that the value represents a risk of recurrence based upon both the PSMA levels and the second method, e.g., Gleason grade and/or cancer stage.

In another aspect, the invention features a method of determining treatment of a subject diagnosed with cancer, e.g., prostate cancer. The method includes: providing a sample obtained from a subject diagnosed with cancer, e.g., prostate cancer; determining PSMA expression levels in the sample, wherein increased PSMA expression levels, e.g., as compared to a reference standard, e.g., levels of a control subject, are indicative of a risk of cancer recurrence; and selecting a treatment based upon the risk of recurrence in the subject.

In one embodiment, the sample can be a biological sample, e.g., a fluid sample (e.g., serum, semen or urine), or a tissue sample, e.g., a tissue from a prostatic or cancerous lesion (e.g., a biopsy sample or a sample obtained from a lesion removed from the subject, e.g., a primary or metastatic lesion). In one embodiment, the subject has prostate cancer and the sample is obtained from a partial or radial prostatectomy from the subject. In another embodiment, the sample is obtained from a biopsy sample. Thus, in some embodiments, the risk of recurrence can be evaluated upon diagnoses of a subject with cancer, e.g., by evaluating a biopsy sample, or can be made after diagnoses, e.g., after a subject being given an anti-cancer treatment, e.g., after a partial or radical prostatectomy. In yet another embodiment, PSMA expression levels can be determined from a fluid sample, e.g., a blood or urine sample. The sample can be obtained before treatment with an anti-cancer therapy, concurrently with treatment, and/or post treatment.

In some embodiments, PSMA protein amounts can be determined using any suitable assay, such as by using an anti-PSMA antibody, e.g., in an enzyme linked immunosorbant assay (ELISA), a radioimmunoassay (RIA), a Western blot or an immunohistochemical method. Alternatively, the level of PSMA expression can be determined by the amount of PSMA nucleic acid (e.g., mRNA) in the biological sample. For example, PSMA nucleic acids expression (e.g., mRNA levels) amounts can be readily determined using any suitable assay, such as Northern blotting, RT-PCR, or the use of biochips.

In some embodiments, the risk of recurrence in a subject having increased PSMA expression levels is greater than 50%, 60%, 65%, 70%, 75%, 80% or more.

In one embodiment, the PSMA levels in the subject are not increased (i.e., are not increased by a statistically significant amount) as compared to the reference control and the treatment selected is one or more of: surgery (e.g., a partial or radical prostatectomy), cryotherapy and radiation therapy.

In another embodiment, the subject's PSMA levels are increased as compared to the reference control and the treatment selected can be, e.g., one or more of: surgery (e.g., partial or radical prostatectomy); radiation therapy (e.g., external-beam therapy; interstitial-radiation therapy; and a combination of external-beam therapy and interstitial-radiation therapy); chemotherapy; antibody therapy (e.g., administration of a labeled and/or an unlabeled antibody, e.g., administration of an anti-PSMA antibody, e.g., an anti PSMA antibody that binds the extracellular domain of PSMA); hormonal therapy, which can be administered alone or can be administered before or following radical prostatectomy or radiation (e.g., treatments that reduce serum testosterone concentrations, or inhibit testosterone activity, e.g., administering a leuteinizing hormone-releasing hormone (LHRH) analog or agonist (e.g., Lupron, Zoladex, leuprolide, buserelin, or goserelin) or antagonists (e.g., Abarelix). Non-steroidal antiandrogens, e.g., flutamide, bicalutimade, or nilutamide, can also be used in hormonal therapy, as well as steroidal antiandrogens (e.g., cyproterone acetate or megastrol acetate), estrogens (e.g., diethylstilbestrol), PROSCAR™, secondary or tertiary hormonal manipulations (e.g., involving corticosteroids (e.g., hydrocortisone, prednisone, or dexamethasone), ketoconazole, and/or aminogluthethimide), inhibitors of 5a-reductase (e.g., finisteride), herbal preparations (e.g., PC-SPES), hypophysectomy, and adrenalectomy. Furthermore, hormonal therapy can be performed intermittently or using combinations of any of the above treatments, e.g., combined use of leuprolide and flutamide.

In some embodiments, when the subject's PSMA levels are increased as compared to the reference control, two or more treatments for the subject are selected. For example, the treatments selected can be: surgery (e.g., a partial or radical prostatectomy), cryotherapy and/or radiation and one or more of: chemotherapy; antibody therapy (e.g., administration of a labeled and/or an unlabeled antibody, e.g., administration of an anti-PSMA antibody, e.g., an anti PSMA antibody that binds the extracellular domain of PSMA) and hormonal therapy.

In some embodiments, when the subject has prostate cancer and the subject's PSMA levels are increased as compared to the reference control, the treatment is a prostatectomy (e.g., a partial or radical prostatectomy) and one or more of: chemotherapy, radiation therapy, hormone therapy, and antibody therapy (e.g., administration of an anti-PSMA antibody, e.g., an anti PSMA antibody that binds the extracellular domain of PSMA). In preferred embodiments, when the subject has prostate cancer and the subject's PSMA levels are increased as compared to the reference control, the treatment includes a prostatectomy (e.g., a radical or partial prostatectomy) and antibody therapy (e.g., with an antibody that binds the extracellular domain of PSMA, e.g., a labeled or unlabeled antibody that binds the extracellular domain of PSMA).

In some embodiments, the method further includes providing a result of the evaluation and the selected treatment to a third party, e.g., a hospital, clinic, government entity, reimbursing party or insurance company. In other embodiments, payment for a medical procedure, e.g., a treatment, or payment by a reimbursing party, e.g., a government entity or insurance company, is conditional on a selected outcome of the evaluation method or a selected treatment based upon the evaluation.

In some embodiments, the method further includes evaluating risk of recurrence by a second method, e.g., by assessing the Gleason grade of the cancer and/or assessing the stage of the cancer. In some embodiments, the method further includes modifying the treatment regimen selected for the subject such that the treatment represents risk of recurrence based upon both the PSMA levels and the second method, e.g., Gleason grade and/or cancer stage.

In another aspect, the invention features a method of selecting subjects for an anti-cancer treatment, e.g., administration of an anti-PSMA antibody. The method includes: determining PSMA expression levels in a plurality of subjects, wherein increased PSMA expression levels, e.g., as compared to a reference standard, are indicative of a risk of cancer recurrence; and selecting a subset of the plurality of subjects having increased expression levels for administration of the anti-cancer treatment, e.g., administration of an anti-PSMA antibody.

In another aspect, the invention features a kit for evaluating cancer recurrence that includes an anti-PSMA antibody, e.g., an anti-PSMA antibody described herein, and information regarding the reference standard. The kit can further include instructions for use. Instructions for use can include instructions for applications of the anti-PSMA antibodies (or antigen-binding fragment thereof) to detect PSMA, in vitro, e.g., in a sample, e.g., a biopsy or cells from a patient having a cancer, e.g., prostate cancer, or in vivo. The instructions can further include information regarding suggested anti-cancer treatments based upon the evaluated risk, and/or suggested dosages and/or modes of administration of the selected treatment, e.g., in a patient with a cancer, e.g., prostate cancer. In some embodiments, the antibody can be labeled, e.g., directly or indirectly labeled or the kit can include a label and instructions for labeling the antibody.

In another aspect, the invention features a kit for evaluating cancer recurrence that includes probes and/or primers that bind to PSMA, e.g., a probe or primer described herein, and information regarding the reference standard. The kit can further include instructions for use. Instructions for use can include instructions for, e.g., PCR, e.g., RT-PCR. The instructions can further include information regarding suggested anti-cancer treatments based upon the evaluated risk, and/or suggested dosages and/or modes of administration of the selected treatment, e.g., in a patient with a cancer, e.g., prostate cancer. In some embodiments, the probe can be labeled, e.g., directly or indirectly labeled or the kit can include a label and instructions for labeling the probe.

In another aspect, the invention features, a method of making a decision, e.g., a medical or financial decision. The method includes: generating or receiving data on the likelihood or risk recurrence of prostate cancer in a patient, e.g., receiving the PSMA level data generated by a method described herein; and using the data to make the decision, e.g., selecting between a first outcome and a second outcome.

In a preferred embodiment, the data is an indicator of the risk of recurrence of prostate cancer.

In a preferred embodiment, the decision is made by comparing the data to a reference standard and making the decision based on the relationship of the data to the reference. For example, the data can be a value or other term for the likelihood of recurrence and if the value or other term has a preselected relationship to the reference standard, e.g., if the value or term in the data is greater than a reference standard, selecting a first outcome and if the data is less than a reference standard selecting a second outcome. An outcome can be providing or not providing service or treatment or paying for or not paying for all or part of a service or treatment.

In a preferred embodiment, the first outcome is suggesting or providing a first course of medical treatment, e.g., any treatment described herein, and the second course is suggesting that the treatment not be given or not providing the treatment.

In a preferred embodiment the first outcome includes or results in the authorization or transfer of funds to pay for a service or treatment provided to a subject and the second outcome includes or results in the refusal to pay for a service or treatment provided to a subject. For example, an entity, e.g., a hospital, care giver, government entity, or an insurance company or other entity that pays for, or reimburses medical expenses, can use the outcome of a method described herein to determine whether a party, e.g., a party other than the subject patient, will pay for services or treatment provided to the patient. For example, a first entity, e.g., an insurance company, can use the outcome of a method described herein to determine whether to provide financial payment to, or on behalf of, a patient, e.g., whether to reimburse a third party, e.g., a vendor of goods or services, a hospital, physician, or other care-giver, for a service or treatment provided to a patient. For example, a first entity, e.g., an insurance company, can use the outcome of a method described herein to determine whether to continue, discontinue, enroll an individual in an insurance plan or program, e.g., a health insurance or life insurance plan or program.

In another aspect, the invention features a method of providing a database, e.g., a database useful for establishing a reference value referred to herein or for otherwise evaluating PSMA levels in one or more subjects. The method includes: generating or receiving data, e.g., PSMA level, on the likelihood or risk recurrence of prostate cancer in a patient, which data is generated by a method described herein; and entering the data into the database.

In a preferred embodiment, one or more of, an indicator (e.g., a value) for the disease state of a patient and a patient identifier are entered into the database.

In a preferred embodiment, the database includes a plurality of entries, each one of which includes one or more of: data (e.g., PSMA expression levels) on the likelihood or risk of recurrence of prostate cancer in a patient; an indicator for the disease state of a patient and a patient identifier.

In another aspect, the invention features a method of evaluating a patient that includes: comparing data from the patient (e.g., PSMA expression levels) on the likelihood or risk recurrence of prostate cancer in a patient, wherein the data was generated by a method described herein, with data from a database described herein.

In another aspect, the invention features a method of constructing a reference standard that includes: including data from a database described herein in the standard. For example, one can take values from a database, perform a mathematical operation on them and use the result as a reference in arriving at a reference standard, e.g., taking an average of a plurality of values selected from the database and use the average as the standard.

As can be seen, e.g., in Example 2, described below, PSMA can be expressed on other tissues such as central nervous system (CNS), peripheral nervous system (PNS), epididymus and salivary gland. Thus, in another aspect, the invention can feature methods of using PSMA binding agents, e.g., anti-PSMA antibodies (and antibody conjugates) such as those described herein and in U.S. Pat. Nos. 6,150,508, 6,107,090 and 6,136,311, PCT Publication No: WO 02/098897, PCT Publication No: WO 01/09192, PCT Publication No: WO 97/35616, U.S. Patent Application Publication No. 2003034903, and Schülke et al., (2003) PNAS USA, 100(27): 12590-12595; Graver et al., (1998) Cancer Res. 58:4787-4789 (the contents of which are incorporated herein by reference), to identify, bind, label, and/or target a tissue from normal or diseased CNS, PNS, epididymis or the salivary gland. The subject method can be used on cells in culture, e.g. in vitro or ex vivo. For example, PSMA-expressing cells of the CNS, PNS, salivary gland or epididymis (e.g., malignant or normal, benign or hyperplastic PSMA expressing cells) can be cultured in vitro in culture medium and the contacting step can be effected by adding an PSMA binding agent, e.g., an anti-PSMA antibody or fragment thereof, to the culture medium. The method can be performed on PSMA expressing cells present in a subject, as part of an in vivo (e.g., therapeutic or prophylactic) protocol. For in vivo embodiments, the contacting step is effected in a subject and includes administering a PSMA binding agent, e.g., an anti-PSMA antibody or fragment thereof, to the subject under conditions effective to permit binding of the antibody or fragment to the cell. Such methods can be used, e.g., for screening, diagnostic and/or therapeutic or prophylactic methods. The methods and PSMA binding agents, e.g., anti-PSMA antibodies, can also be used to treat or prevent disorders involving aberrant activity of a PSMA-expressing cell, e.g., a cell of the CNS, a cell of the PNS, a cell of the salivary gland or a cell of the epididymis.

The disorder, e.g., the proliferative disorder, can be a disorder of the CNS. For example, the disorder can effect one or more of the cells or tissues of the CNS including: a portion of the brain (e.g., thalmus, hypothalmus, basal ganglia, cerebrum), neurons (e.g., sensory, motor, secretory and/or an association neuron), glial cells (e.g., astrocytes, microglia, macroglia and oligodendricytes).

The disorder, e.g., the proliferative disorder, can be a disorder of the PNS. For example, the disorder can effect one or more of the cells or tissues of the PNS including: neurons, e.g., spinal and/or cranial neuron (e.g., sensory, motor, secretory and/or an association neuron), ganglia, connective tissue, and glial cells (e.g., Schwann cells, satellite cells, susentecular cells, macroglia, astrocytes, microglia, oligodendricytes).

The disorder, e.g., the proliferative disorder, can be a disorder of the salivary gland. For example, the disorder can effect one or more of the cells or tissues of the salivary gland including: acenar cells, myoepithelial cells, duct cells (e.g., striated, intercalated or exorectory), and connective tissue.

The disorder, e.g., the proliferative disorder, can be a disorder of the epididymis. For example, the disorder can effect one or more of the cells or tissues of the epididymis including: epithelial cells, muscle cells and duct cells.

DETAILED DESCRIPTION OF THE INVENTION

Figure 1A:
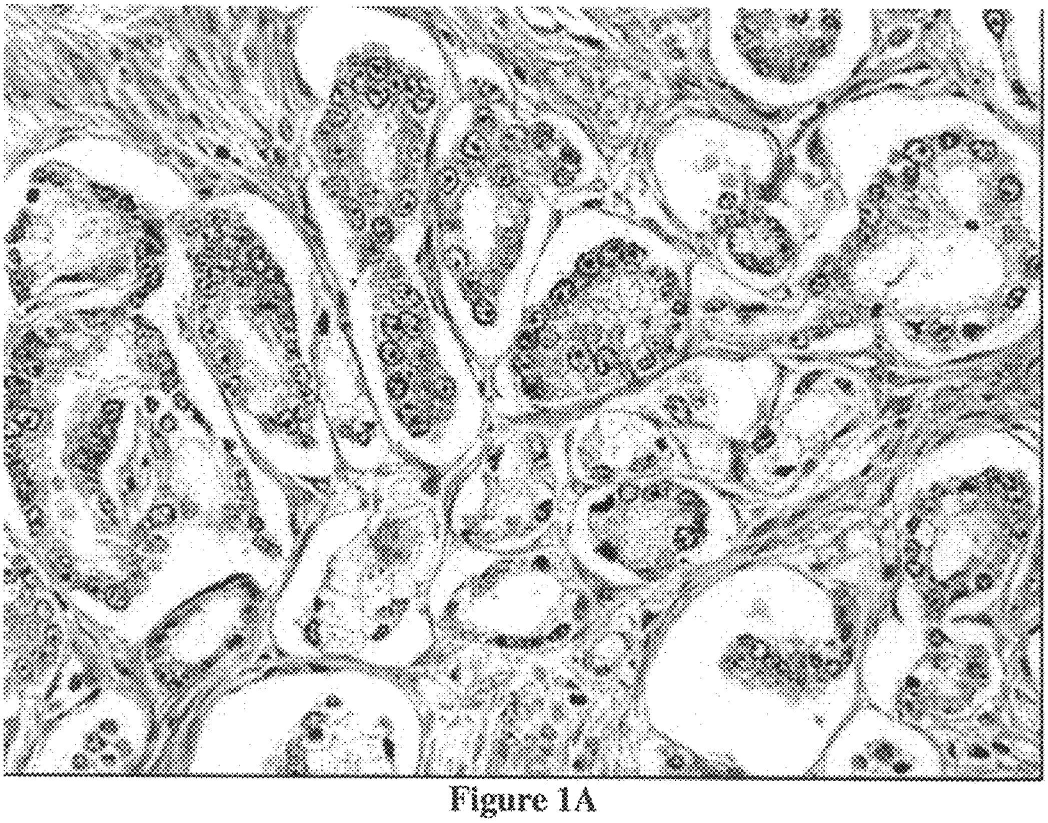
FIG. 1A is a photograph showing relatively weak PSMA immunostaining in a 64 year old Caucasian man with a Stage III-extra-capsular Gleason 7 prostate cancer that has not recurred at 68 months of observation/(anti-PSMA with 7E11 antibody, peroxidase-antiperoxidase with hematoxylin counterstain X 200).

Despite the current interest in PSMA as a target of therapy for patients with HRPC, PSMA expression in prostate cancer has not previously been evaluated as a stand-alone prognostic marker. As shown in the Examples below, PSMA expression status can be used as a predictor of prostate cancer disease outcome. This was done by correlating cytoplasmic immunoreactivity for PSMA protein to tumor grade, stage, DNA ploidy status (Feulgen spectroscopy) and biochemical disease recurrence. In addition, other molecular techniques (transcriptional profiling (TP) using cDNA microarrays on nylon membranes, RT-PCR (TaqMan), in situ hybridization, laser capture microdissection (LCM), and Western blotting) were used to evaluate the regulation of RNA and protein in various stages of PCA development and progression.

It was found that PSMA mRNA and protein expression are highly restricted to normal prostate and prostate cancer tissues with elevated levels of mRNA in a subset of PCAs and metastases, and increases in immunoreactive PSMA protein as the tumor progresses from localized to metastatic disease. It was also found that over-expression of PSMA protein in the tumor independently predicts disease outcome. There are a number major obstacles to overcome in considering a target as a candidate for monoclonal antibody therapy that include: clinical relevance of the target, tumor specificity, heterogeneity of expression, internalization, shedding of antigen, and biological activity of target. This study demonstrates a prostate gland restricted and epithelial specificity for PSMA with further upregulation of PSMA at the mRNA and protein level in a significant number of malignant lesions, and a clinically relevant association of PSMA protein overexpression with aggressive disease and relatively poor prognosis.

In order that the present invention may be more readily understood, certain terms are first defined. Additional definitions are set forth throughout the detailed description.

As used herein, "PSMA" or "prostate-specific membrane antigen" protein refers to mammalian PSMA, preferably human PSMA protein and dimers thereof. Human PSMA includes the two protein products, PSMA and PSM', encoded by the two alternatively spliced mRNA variants (containing about 2,653 and 2,387 nucleotides, respectively) of the PSMA cDNA disclosed in Israeli et al. (1993) *Cancer Res.* 53:227-230; Su et al. (1995) *Cancer Res.* 55:1441-1443; U.S. Pat. No. 5,538,866, U.S. Pat. No. 5,935,818, and WO 97/35616, the contents of which are hereby incorporated by reference. The long transcript of PSMA encodes a protein product of about 100-120 kDa molecular weight characterized as a type II transmembrane receptor having sequence homology with the transferrin receptor and having NAALADase activity (Carter et al. (1996) *Proc. Natl. Acad. Sci. USA* 93:749-753). Accordingly, the term "human PSMA" refers to at least two protein products, human PSMA and PSM', which have or are homologous to (e.g., at least about 85%, 90%, 95% identical to) an amino acid sequence:

MetTrpAsnLeuLeuHisGluThrAspS-
erAlaValAlaThrAlaArgArgProArgTrpLeuCysAlaGly Ala-
LeuValLeuAlaGlyGlyPhePh-
eLeuLeuGlyPheLeuPheGlyTrpPheIleLysSerSerAsnGlu
AlaThrA snIleThrProLysHisAsnMetLysAl-
aPheLeuAspGluLeuLysAlaGluAs-
nIleLysLysPheLeuTyrAsnPh eThrGlnIleProHisLeuAlaG-
lyThrGluGlnAsnPheGlnLeuAlaLysGlnIleGlnSerGlnTrp
LysGluPheG lyLeuAspSerValGluLeuAla-
HisTyrAspValLeuLeuSerTyr-
ProAsnLysThrHisProAsnTyrIleSerIleIl eAsnGluAspGlyAs-
nGluIlePheAsnThrSerLeuPheGluProProProProGlyTyr
GluAsnValSerAspIle ValProProPheSerAlaPheSerPro-
GlnGlyMetProGluGlyAspLeuVal-
TyrValAsnTyrAlaArgThrGluA spPhePheLysLeuGluAr-
gAspMetLysIleAsnCysSerGlyLysIleValIleAlaArgTyrGly
LysValPheArg GlyAsnLysValLysAsnAlaGln-
LeuAlaGlyAlaLysGlyValIleLeu-
TyrSerAspProAlaAspTyrPheAlaP roGlyValLysSerTyr-
ProAspGlyTrpAsnLeuProGlyGlyGlyValGlnArgGlyAsnIle
LeuAsnLeuAsnG lyAlaGlyAspProLeuThrProGly-
TyrProAlaAsnGluTyrAlaTyrAr-
gArgGlyIleAlaGluAlaValGlyLeu ProSerIleProValHisProI-
leGlyTyrTyrAspAlaGlnLysLeuLeuGluLysMetGlyGlySer
AlaProProAsp SerSerTrpArgGlySerLeuLysVal-
ProTyrAsnValGlyProGlyPheThrG-
lyAsnPheSerThrGlnLysValL ysMetHisIleHisSerThrAsn-
GluValThrArgIleTyrAsnValIleGlyThrLeuArgGlyAlaVal
GluProAspA rgTyrValIleLeuGlyGlyHisAr-
gAspSerTrpValPheGlyGlyIleAsp-
ProGlnSerGlyAlaAlaValValHisG luIleValArgSerPheGlyTh-
rLeuLysLysGluGyTrpArgProArgArgThrIleLeuPheAlaSer
TrpAspAla GluGluPheGlyLeuLeuGlySerThr-
GluTrpAlaGluGluAsnSerAr-
gLeuLeuGlnGluArgGlyValAlaTyr IleAsnAlaAspSerSerIle-
GluGlyAsnTyrThrLeuArgValAspCysThrProLeuMetTyr
SerLeuValHisAs nLeuThrLysGluLeuLysSerProAsp-
GluGlyPheGluGlyLysSerLeuTyr-
GluSerTrpThrLysLysSerPro SerProGluPheSerGlyMet-
ProArgIleSerLysLeuGlySerGlyAsnAspPheGluValPhePhe
GlnArgLeuG lyIleAlaSerGlyArgAlaArg-
TyrThrLysAsnTrp-
GluThrAsnLysPheSerGlyTyrProLeuTyrHisSerVal Tyr-
GluThrTyrGluLeuValGluLysPheTyrAspProMetPheLys
TyrHisLeuThrValAlaGlnValArgGly GlyMetValPheG-
luLeuAlaAsnSerIleValLeuProPh-
eAspCysArgAspTyrAlaValValLeuArgLysTyr AlaAspLysI-
leTyrSerIleSerMetLysHisProGlnGluMetLysThrTyrSerVal
SerPheAspSerLeuPheSer AlaValLysAsnPheThrGluIleAla-
SerLysPheSerGluArgLeuGlnAsp-
PheAspLysSerAsnProIleValLe uArgMetMetAsnAspGln-
LeuMetPheLeuGluArgAlaPheIleAspProLeuGlyLeuPro
AspArgProPheT yrArgHisValIleTyrAlaProS-
erSerHisAsnLysTyrAlaGly-
GluSerPheProGlyIleTyrAspAlaLeuPheA spIleGluSerLysV-
alAspProSerLysAlaTrpGlyGluValLysArgGlnIleTyrVal
AlaAlaPheThrValGlnA laAlaAlaGluThrLeuSerGluValAla
(SEQ ID NO:1) or

MetLysAlaPheLeuAspGluLeu-
LysAlaGluAsnIleLysLysPheLeu-
TyrAsnPheThrGlnIleProHisLeu AlaGlyThrGluGlnAsn-
PheGlnLeuAlaLysGlnIleGlnSerGlnTrpLysGluPheGlyLeu
AspSerValGluL euAlaHisTyrAspValLeuLeuSer-
TyrProAsnLysThrHisProAsnTyr-
IleSerIleIleAsnGluAspGlyAsnG luIlePheAsnThrSerLe-
uPheGluProProProProGlyTyrGluAsnValSerAspIleValPro
ProPheSerAlaPh eSerProGlnGlyMetProGluGlyAs-
pLeuValTyrValAsnTyrAlaArgThr-
GluAspPhePheLysLeuGluAr AlaGlnLeuAlaGlyAlaLysGly-
ValIleLeuTyrSerAspProAlaAspTyrPheAlaProGlyValLys
SerTyrPr oAspGlyTrpAsnLeuProGlyGlyGly-
ValGlnArgGlyAsnIleLeuAsn-

LeuAsnGlyAlaGlyAspProLeuT hrProGlyTyrProAlaAsn-GluTyrAlaTyrArgArgGlyIleAlaGluAlaValGlyLeuProSer IleProValHisPr oIleGlyTyrTyrAspAla-GlnLysLeuLeuGluLysMetGlyGly-SerAlaProProAspSerSerTrpArgGlySerL euLysValPro-TyrAsnValGlyProGlyPheThrGlyAsnPheSerThrGlnLys ValLysMetHisIleHisSerThr AsnGluValThrArgIleTyrAsn-ValIleGlyThrLeuArgGlyAlaValG-luProAspArgTyrValIleLeuGlyGl yHisArgAspSerTrpVal-PheGlyGlyIleAspProGlnSerGlyAlaAlaValValHisGluIle ValArgSerPheGl yThrLeuLysLysGluGlyTrpArg-ProArgArgThrIleLeuPheAlaSer-TrpAspAlaGluGluPheGlyLeuLeu GlySerThrGluTrpAla-GluGluAsnSerArgLeuLeuGlnGluArgGlyValAlaTyrIleAsn AlaAspSerSerIl eGluGlyAsnTyrThrLeuArgValAsp-CysThrProLeuMetTyrSerLeuVal-HisAsnLeuThrLysGluLeuL ysSerProAspGluGlyPheGluG-lyLysSerLeuTyrGluSerTrpThrLysLysSerProSerProGluPhe SerGly MetProArgIleSerLysLeuGlySerG-lyAsnAspPheGluValPheP-heGlnArgLeuGlyIleAlaSerGlyArgAl aArgTyrThrLysAsn-TrpGluThrAsnLysPheSerGlyTyrProLeuTyrHisSerValTyr GluThrTyrGluLeu ValGluLysPheTyrAspProMet-PheLysTyrHisLeuThrValAlaGln-ValArgGlyGlyMetValPheGluLeu AlaAsnSerIleValLeu-ProPheAspCysArgAspTyrAlaValValLeuArgLysTyrAla AspLysIleTyrSerIle SerMetLysHisProGlnGlu-MetLysThrTyrSerValSerPheAspS-erLeuPheSerAlaValLysAsnPheThrG luIleAlaSerLysPhe-SerGluArgLeuGlnAspPheAspLysSerAsnProIleValLeu ArgMetMetAsnAspGl nLeuMetPheLeuGluArgAlaPheI-leAspProLeuGlyLeuProAspArg-ProPheTyrArgHisValIleTyrAla ProSerSerHisAsnLy-sTyrAlaGlyGluSerPheProGlyIleTyrAspAlaLeuPheAspIle GluSerLysValAsp ProSerLysAlaTrpGlyGlu-ValLysArgGlnIleTyrValAlaAl-aPheThrValGlnAlaAlaAlaGluThrLeuSer GluValAla (SEQ ID NO:2); or which is encoded by (a) a naturally occurring human PSMA nucleic acid sequence (e.g., Israeli et al. (1993) *Cancer Res.* 53:227-230 or U.S. Pat. No. 5,538,866); (b) a nucleic acid sequence degenerate to a naturally occurring human PSMA sequence; (c) a nucleic acid sequence homologous to (e.g., at least about 85%, 90%, 95% identical to) the naturally occurring human PSMA nucleic acid sequence; or (d) a nucleic acid sequence that hybridizes to one of the foregoing nucleic acid sequences under stringent conditions, e.g., highly stringent conditions.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), *J. Mol. Biol.* 48:444-453, algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a homology limitation of the invention) are a Blossum 62 scoring matrix with a gap penalty of 12, a gap extend penalty of 4, and a frameshift gap penalty of 5.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

"Recurrence" as used herein refers to an increase in PSA levels after an anti-cancer treatment (e.g., prostatectomy or radiation) to greater than 0.4 ng/dL in two consecutive tests spaced by a one month period. After an anti-cancer treatment such as a prostatectomy or radiation, PSA levels drop to low and in some cases undetectable levels in the blood. This drop in PSA levels below 0.4 ng/dL allows PSA levels to be followed in order to determine if there has been cancer recurrence in a subject. Cancer recurrence can occur over a short period of time from the anti-cancer treatment, e.g., a few months after treatment, or can occur several years after an anti-cancer treatment. For example, in prostate cancer patients, recurrence can happen several years after an anticancer treatment, e.g., up to 4, 5, 6, 7, 8, 9, 10, 12, 14, 15 years after treatment. Recurrence can be classified as "local recurrence" or "distant recurrence". "Local recurrence" refers to cancers that recur in tissue or organs adjacent to or proximate to the cancerous tissue or organ. For example, in subjects having prostate cancer, local recurrence can occur in tissue next to the prostate, in the seminal vesicles, the surrounding lymph nodes in the pelvis, the muscles next to the prostate, and the rectum and/or walls of the pelvis. "Distant recurrence" refers to cancers that recur distant from the cancerous tissue or organ. For example, in subjects having prostate cancer, distant recurrence includes cancers that spread to the bones or other organs.

Other methods are known for assessing risk of recurrence. For example, in subjects having prostate cancer, risk of recurrence can be evaluated by several different methods including one or more of: determining the grade of the cancer; determining the stage of the cancer; and determining the DNA ploidy status (e.g., determining the DNA index).

The "grade" of the cancer or the "Gleason grade" as used herein, refers to a pathological analysis of a sample, e.g., a biopsy sample, obtained from a subject. Methods of determining Gleason grade are described, e.g., in Gleason (1992) *Hum Pathol.* 23:273-279. Briefly, the appearance of cancer cells are compared to the appearance of normal prostate tissue, and the cancer cells are designated a grade from 1 to 5. Grade 1 represents cells that are almost normal as compared to normal prostate tissue. Grade 5 are the worst and designate cells that have a very abnormal pathology as compared to normal prostrate tissue. The results from the two greatest areas of cancer in the sample, e.g., the biopsy sample, are added up to give the Gleason grade. Therefore, positive samples can have a Gleason grade from Grade 2 to Grade 10. A Gleason grade of 6 to 7 is considered moderate.

The "stage" of a cancer as used herein refers to how far the cancer has progressed. Methods of determining the stage of a cancer are described, e.g., in Ohori et al. (1994) *Cancer* 74:104-114. The most common staging systems assigns stages of I, II, III and IV to a cancer. For prostate cancer, "Stage I" refers to a cancer that is only found by elevated PSA and biopsy, or at surgery for an obstruction. Stage I cancers are localized to the prostate. "Stage II" refers to a cancer that can be felt upon rectal examination and is limited to the prostate. Stage II cancers may also be evaluated by, e.g., bone scan, and/or CT/MRI scan. "Stage III" refers to a cancer that has spread beyond the capsule of the prostate into the local organs and/or tissue, but has not yet metastasized. Stage III cancers can be diagnosed, e.g., using digital rectal examination, CT/MRI scans, and/or sonography. "Stage IV" refers to a cancer that has spread, usually to distant lymph nodes, bone and other sites. Stage 1V cancers can be diagnosed, e.g., using a bone scan and/or Prostascint scan.

Methods of determining the DNA index are evaluated, e.g., by determining the if the tumor is diploid or non-diploid. A method of determining DNA index is provided, e.g., in Example 1.

Evaluating PSMA Expression

The invention relates to predictive medicine using PSMA expression as a determinant of risk of cancer recurrence. Contemplated within the scope of this invention is the implementation of PSMA expression analysis as a part of a pharmacogenetic protocol (e.g., using biochips) for evaluating patient status and prognosis.

The level of mRNA corresponding to the PSMA gene in a cell can be determined, e.g., by in situ or in vitro formats.

PSMA mRNA probes can be used in hybridization or amplification assays that include, but are not limited to, Southern or Northern analyses, polymerase chain reaction analyses and probe arrays. One method for the detection of mRNA levels involves contacting the mRNA with a nucleic acid molecule (probe) that can hybridize to the mRNA encoded by the gene being detected. The nucleic acid probe can be, for example, a full-length PSMA nucleic acid or a portion thereof, such as an oligonucleotide of at least 7, 10, 15, 30, 50, 100, 250 or 500 nucleotides in length and sufficient to hybridize under stringent conditions to PSMA mRNA, cDNA, or portions thereof. The probes can be labeled with a detectable reagent to facilitate identification of the probe. Useful reagents include, but are not limited to, radioactivity, fluorescent dyes or enzymes capable of catalyzing a detectable product.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the PSMA gene.

The level of mRNA in a sample that is encoded by a PSMA nucleic acid can be evaluated with nucleic acid amplification, e.g., by RT-PCR (U.S. Pat. No. 4,683,202), ligase chain reaction (Barany, Proc. Natl. Acad. Sci. USA 88:189-193, 1991), self sustained sequence replication (Guatelli et al., Proc. Natl. Acad. Sci. USA 87:1874-1878, 1990), transcriptional amplification system (Kwoh et al., Proc. Natl. Acad. Sci. USA 86:1173-1177, 1989), Q-Beta Replicase (Lizardi et al., Bio/Technology 6:1197, 1988), rolling circle replication (U.S. Pat. No. 5,854,033), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule including the nucleotide sequence flanked by the primers.

For in situ methods, a cell or tissue sample can be prepared/processed and immobilized on a support, typically a glass slide, and then contacted with a probe that can hybridize to mRNA that encodes the PSMA gene being analyzed.

A variety of methods can be used to determine the level of protein encoded by the PSMA gene. In general, these methods include contacting an agent that selectively binds to the protein, such as an antibody, with a sample to evaluate the level of protein in the sample. In one embodiment, the antibody includes a detectable label. Antibodies can be polyclonal or monoclonal. An intact antibody, or a fragment thereof (e.g., Fab or $F(ab')_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of antibodies that can be used to detect PSMA include, e.g., 7E11 (which binds to the intracellular domain of PSMA) as well as any of the antibodies described in U.S. Pat. Nos. 6,150,508, 6,107,090 and 6,136,311, PCT Publication No: WO 02/098897, PCT Publication No: WO 97/35616, and PCT Publication No: WO 01/09192, U.S. Patent Application Publication No. 2003034903, Schülke et al., (2003) *PNAS USA,* 100(27):12590-12595; Graver et al., (1998) *Cancer Res.* 58:4787-4789 (the contents of which are incorporated herein by reference).

The detection methods can be used to detect PSMA protein in a biological sample in vitro as well as in vivo. In vitro techniques for detection of PSMA protein include enzyme linked immunosorbent assays (ELISAs), immunoprecipitations, immunofluorescence, enzyme immunoassays (EIA), radioimmunoassays (RIA), and Western blot analysis. In vivo techniques for detection of PSMA protein include introducing into a subject a labeled anti-PSMA antibody. For example, the antibody can be labeled with a radioactive marker, e.g., a radioisotope) whose presence and location in a subject can be detected by standard imaging techniques. A radioisotope can be an α-, β-, or γ-emitter, or an β- and γ-emitter. Examples of radioisotopes that can be used include, but are not limited to: yttrium ($^{90}Y$), lutetium ($^{177}Lu$), actinium ($^{225}Ac$), praseodymium, astatine ($^{211}At$), rhenium ($^{186}Re$), bismuth ($^{212}Bi$ or $^{213}Bi$), and rhodium ($^{188}Rh$). Radioisotopes useful as labels, e.g., for use in diagnostics, include iodine ($^{131}I$ or $^{125}I$), indium ($^{111}In$), technetium ($^{99}mTc$), phosphorus ($^{32}P$), carbon ($^{14}C$), and tritium ($^{3}H$).

In some embodiments, the methods include comparing the level of PSMA expression to a reference standard. The term "reference standard" as used herein can refer to a standard that is a statistically significant level of PSMA expression which distinguishes subjects having recurrence and subjects that do not have recurrence. The standard can be a particular level of PSMA expression. A skilled artisan can provide a reference standard by taking a measurement of PSMA expression levels in subjects having recurrence and subjects that do not have recurrence to define the standard. For example, as described herein in Example 1, a determination of PSMA over-expression can be compared to a reference standard using immunohistochemical analysis. Briefly, the staining of a sample, e.g., a biopsy sample or sample from a prostatectomy, can be evaluated for the intensity of staining and the distribution of cytoplasmic staining from immunohistochemical results. The distribution of staining was graded as focal, regional or diffuse. The intensity of staining was classified as weak, moderate or intense. Cases where the staining pattern was categorized as intense diffuse, intense regional or moderate diffuse were considered to be over-expressing the PSMA protein. Methods such as this can be used to determine whether there is a statistically significant increase in PSMA expression in those subjects having recurrence. In some embodiments, the increase is at least about 100% of the level of the reference standard, i.e., the level of expression in the sample is twice the level of expression in the reference standard, e.g., expression is increased by 150%, 200%, 250%, 300%, or more.

Anti-Cancer Treatments

The methods can further include selecting a treatment for a subject diagnosed with cancer, or selecting a population of subjects diagnosed with cancer for a particular treatment, by assessing the risk of recurrence in the subject or subjects.

As used herein, the term "treat" or "treatment" is defined as the application or administration of a cancer modality to a subject, e.g., a patient, or application or administration to an isolated tissue or cell from a subject, e.g., a patient, which is returned to the patient. Depending on the risk of recurrence determined, one or more treatment can be administered to a subject. The subject can be a patient having a disorder (e.g., a disorder as described herein), or a symptom of a disorder. The treatment can be to cure, heal, alleviate, relieve, alter, remedy, ameliorate, palliate, improve or affect the disorder, or the symptoms of the disorder.

Examples of existing anti-cancer treatments that can be selected, include, but not limited to: surgery (e.g., radical prostatectomy); radiation therapy (e.g., external-beam therapy which involves three dimensional, conformal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy); hormonal therapy, which can be administered before or following radical prostatectomy or radiation (e.g., treatments that reduce serum testosterone concentrations, or inhibit testosterone activity, e.g., administering a leuteinizing hormone-releasing hormone (LHRH) analog or agonist (e.g., Lupron, Zoladex, leuprolide, buserelin, or goserelin) or antagonists (e.g., Abarelix). Non-steroidal anti-androgens, e.g., flutamide, bicalutimade, or nilutamide, can also be used in hormonal therapy, as well as steroidal anti-androgens (e.g., cyproterone acetate or megastrol acetate), estrogens (e.g., diethylstilbestrol), PROSCAR™, secondary or tertiary hormonal manipulations (e.g., involving corticosteroids (e.g., hydrocortisone, prednisone, or dexamethasone), ketoconazole, and/or aminogluthethimide), inhibitors of 5a-reductase (e.g., finisteride), herbal preparations (e.g., PC-SPES, see U.S. Ser. No. 08/697,920), hypophysectomy, and adrenalectomy. Furthermore, hormonal therapy can be performed intermittently or using combinations of any of the above treatments, e.g., combined use of leuprolide and flutamide.

In addition to the above treatments, the treatment selected can be administration of an anti-PSMA antibody, e.g., a labeled or unlabeled anti-PSMA antibody. An "anti-PSMA antibody" is an antibody that interacts with (e.g., binds to) PSMA, preferably human PSMA protein. Preferably, the anti-PSMA antibody interacts with, e.g., binds to, the extracellular domain of PSMA, e.g., the extracellular domain of human PSMA located at about amino acids 44-750 of human PSMA (amino acid residues correspond to the human PSMA sequence disclosed in U.S. Pat. No. 5,538,866). In one embodiment, the anti-PSMA antibody binds all or part of the epitope of an antibody described in U.S. Pat. Nos. 6,150,508, 6,107,090 and 6,136,311, PCT Publication WO 97/35616, and PCT Publication No: WO 02/098897, U.S. Patent Application Publication No. 2003034903, Schülke et al., (2003) *PNAS USA,* 100(27):12590-12595; Graver et al., (1998) Cancer Res. 58:4787-4789 (the contents of which are incorporated herein by reference), e.g., one or more of J591, E99, J415, J533 or fragments thereof. The anti-PSMA antibody can inhibit, e.g., competitively inhibit, the binding of an antibody anti-PSMA antibody such as J591, E99, J415, and J533, to human PSMA. An anti-PSMA antibody may bind to an epitope, e.g., a conformational or a linear epitope, which epitope when bound prevents binding of an antibody anti-PSMA antibody such as J591, E99, J415, and J533. The epitope can be in close proximity spatially or functionally-associated, e.g., an overlapping or adjacent epitope in linear sequence or conformationally to the one recognized by the J591, E99, J415, or J533 antibody. In one embodiment, the anti-PSMA antibody binds to an epitope located wholly or partially within the region of about amino acids 120 to 500, preferably 130 to 450, more preferably, 134 to 437, or 153 to 347, of human PSMA (amino acid residues correspond to the human PSMA sequence disclosed in U.S. Pat. No. 5,538, 866). Preferably, the epitope includes at least one glycosylation site, e.g., at least one N-linked glycosylation site (e.g., an asparagine residue located at about amino acids 190-200, preferably at about amino acid 195, of human PSMA; amino acid residues correspond to the human PSMA sequence disclosed in U.S. Pat. No. 5,538,866). In some embodiments, the antibodies (or fragments thereof) are a recombinant or modified anti-PSMA antibody chosen from, e.g., a chimeric, a humanized, a deimmunized, or an in vitro generated antibody such as those described in PCT Publication No: WO 02/098897. In other embodiments, the antibodies (or fragments thereof) are human anti-PSMA antibodies such as those described in PCT Publication No.: WO 01/09192.

When an anti-PSMA antibody is selected as the treatment, the anti-PSMA antibody, e.g., a modified anti-PSMA antibody, or antigen-binding fragment thereof, described, e.g., in U.S. Pat. Nos. 6,107,090 and 6,136,311, and PCT Publication No: WO 02/098897, e.g., can be administered to a subject, or used in vitro, in non-derivatized or unconjugated forms. In other embodiments, the anti-PSMA antibody, or antigen-binding fragment thereof, can be derivatized or linked to another molecular entity, typically a label or a therapeutic (e.g., a cytotoxic or cytostatic) agent. The molecular entity can be, e.g., another peptide, protein (including, e.g., a viral coat protein of, e.g., a recombinant viral particle), a non-peptide chemical compound, isotope, etc. The anti-PSMA antibody, or antigen-binding fragment thereof, can be functionally linked, e.g., by chemical coupling, genetic fusion, non-covalent association or otherwise, to one or more other molecular entities. For example, the anti-PSMA antibody, or antigen-binding fragment thereof, can be coupled to a label, such as a fluorescent label, a biologically active enzyme label, a radioisotope (e.g., a radioactive ion), a nuclear magnetic resonance active label, a luminescent label, or a chromophore. In other embodiments, the anti-PSMA antibody, or antigen-binding fragment thereof, can be coupled to a therapeutic agent, e.g., a cytotoxic moiety, e.g., a therapeutic drug, a radioisotope, molecules of plant, fungal, or bacterial origin, or biological proteins (e.g., protein toxins) or particles (e.g., recombinant viral particles, e.g., via a viral coat protein), or mixtures thereof. The therapeutic agent can be an intracellularly active drug or other agent, such as short-range radiation emitters, including, for example, short-range, high-energy $\alpha$-emitters, as described herein. In some preferred embodiments, the anti-PSMA antibody, or antigen binding fragment thereof, can be coupled to a molecule of plant or bacterial origin (or derivative thereof), e.g., a maytansinoid (e.g., maytansinol or the DM1 maytansinoid), a taxane, or a calicheamicin. A radioisotope can be an $\alpha$-, $\beta$-, or $\gamma$-emitter, or an $\beta$- and $\gamma$-emitter. Radioisotopes useful as therapeutic agents include yttrium ($^{90}Y$), lutetium ($^{177}Lu$), actinium ($^{225}Ac$), praseodymium, astatine ($^{211}At$), rhenium ($^{186}Re$), bismuth ($^{212}Bi$ or $^{213}Bi$), and rhodium ($^{188}Rh$). Radioisotopes useful as labels, e.g., for use in diagnostics, include iodine ($^{131}I$ or $^{125}I$), indium ($^{111}In$), technetium ($^{99}mTc$), phosphorus ($^{32}P$), carbon ($^{14}C$), and tritium ($^{3}H$), or one of the therapeutic isotopes listed above. The anti-PSMA antibody, or antigen-binding fragment thereof can also be linked to another antibody to form, e.g., a bispecific or a multispecific antibody. Examples of other agents that can be used in an anti-PSMA antibody therapy are described, e.g., in U.S. Pat. Nos. 6,107,090 and 6,136,311, and PCT Publication No: WO 02/098897.

The methods described herein can further be used to select a dose, e.g., a therapeutically effective dose, of an anti-cancer treatment for a subject, e.g., a subject at risk for recurrence. As used herein, an amount of an anti-cancer treatment, e.g., an anti-PSMA antibody, effective to treat a disorder, or a "therapeutically effective amount" refers to an amount of the treatment that is effective, upon single or multiple dose administration to a subject, in treating a cell, e.g., a prostatic or cancer cell (e.g., a PSMA-expressing prostatic or cancer cell, or a vascular cell proximate thereto), or in prolonging curing, alleviating, relieving or improving a subject with a disorder as described herein beyond that expected in the absence of such treatment. As used herein, "inhibiting the growth" of the neoplasm refers to slowing, interrupting, arresting or stopping its growth and metastases and does not necessarily indicate a total elimination of the neoplastic growth.

Many treatment regimens currently used for treating prostate cancer and prostate cancer recurrence include a first treatment such as a prostatectomy or radiation, then only if PSA levels later indicate recurrence, an additional treatment many be given to treat the recurrence. Some methods currently used, e.g., rely on a scan detect a recurrence of prostate cancer that only detect recurrence when a volume of cancer effects changes to normal anatomic structures. This also indicates a significant advance in disease progression. Thus, in some embodiments, the methods described herein can allow a treatment regimen to be chosen that includes not only a treatment to treat the cancer, e.g., a prostatectomy or radiation, but also provides a treatment to prevent future recurrence in those subjects determined to be at risk. As used herein, an amount of an anti-cancer treatment, e.g., an anti-PSMA antibody, effective to prevent a disorder, or a "a prophylactically effective amount" of the treatment refers to an amount of an anti-cancer treatment, e.g., an anti-PSMA antibody, which is effective, upon single- or multiple-dose administration to the subject, in preventing or delaying the recurrence of a disorder, e.g., a cancer or prostatic disorder as described herein, or treating a symptom thereof.

The terms "induce," "inhibit," "potentiate," "elevate," "increase," "decrease" or the like, e.g., which denote quantitative differences between two states, refer to a difference, e.g., a statistically or clinically significant difference, between the two states. For example, "an amount effective to inhibit the proliferation of the PSMA-expressing hyperproliferative cells" means that the rate of growth of the cells will be different, e.g., statistically different, from the untreated cells.

As used herein, the term "cancer" is meant to include all types of cancerous growths or oncogenic processes, metastatic tissues or malignantly transformed cells, tissues, or organs, irrespective of histopathologic type or stage of invasiveness.

Examples of non-prostatic cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx. Adenocarcinomas include malignancies such as most colon cancers, rectal cancer, renal-cell carcinoma, liver cancer, non-small cell carcinoma of the lung, cancer of the small intestine and cancer of the esophagus. Treatment for a metastatic lesions of the aforementioned cancers can also be selected to treat or prevent the disorder based upon an results of an evaluation method described herein.

As described herein, in some embodiments, the method includes selecting more than one treatment for a subject, e.g., a subject determined to be at risk for recurrence. Thus, the methods described herein include selecting combinations of anti-cancer therapies. For example, the combination therapy can include an anti-PSMA antibody coformulated with, and/ or coadministered with, one or more additional therapeutic agents, e.g., one or more anti-cancer agents, cytotoxic or cytostatic agents, hormone treatment, vaccines, and/or other immunotherapies. In other embodiments, the anti-cancer treatment can be administration of an anti-PSMA antibodies in combination with other therapeutic treatment modalities, including surgery, radiation, cryosurgery, and/or thermotherapy. Such combination therapies may advantageously utilize lower dosages of the administered therapeutic agents, thus avoiding possible toxicities or complications associated with the various monotherapies.

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the treatment selected can be administration of an anti-PSMA antibodies in combination with one or more of the existing modalities for treating prostate cancers, including, but not limited to: surgery (e.g., radical prostatectomy); radiation therapy (e.g., external-beam therapy that involves three dimensional, conformal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy); hormonal therapy, which can be administered before or following radical prostatectomy or radiation (e.g., treatments that reduce serum testosterone concentrations, or inhibit testosterone activity, e.g., administering a leuteinizing hormone-releasing hormone (LHRH) analog or agonist (e.g., Lupron, Zoladex, leuprolide, buserelin, or goserelin) or antagonists (e.g., Abarelix). Non-steroidal anti-androgens, e.g., flutamide, bicalutimade, or nilutamide, can also be used in hormonal therapy, as well as steroidal anti-androgens (e.g., cyproterone acetate or megastrol acetate), estrogens (e.g., diethylstilbestrol), PROSCAR™, secondary or tertiary hormonal manipulations (e.g., involving corticosteroids (e.g., hydrocortisone, prednisone, or dexamethasone), ketoconazole, and/or aminogluthethimide), inhibitors of 5a-reductase (e.g., finisteride), herbal preparations (e.g., PC-SPES), hypophysectomy, and adrenalectomy. Furthermore, hormonal therapy can be performed intermittently or using combinations of any of the above treatments, e.g., combined use of leuprolide and flutamide.

In other embodiments, the anti-cancer treatment can be administered in combination with an immunomodulatory agent, e.g., IL-1, 24, 6, or 12, or interferon alpha or gamma. A small number of clinical trials have combined IL-2 with a monoclonal antibody (Albertini et al. (1997) *Clin Cancer Res* 3:1277-1288; Frost et al. (1997) *Cancer* 80:317-333; Kossman et al. (1999) *Clin Cancer Res* 5:2748-2755). IL-2 can be administered by either bolus or continuous infusion. Accordingly, the anti-cancer treatment can be administered in combination with an immunomodulatory agent to maximize their therapeutic potential.

The following invention is further illustrated by the following examples, which should not be construed as further limiting. The contents of all references, pending patent applications and published patents, cited throughout this application are hereby expressly incorporated by reference.

EXAMPLES

Using prostatectomy specimens, immunohistochemical staining (IHC) for PSMA (7E11 antibody) was performed on formalin-fixed paraffin-embedded sections of 136 cases of PCA. Cytoplasmic immunoreactivity was scored for intensity and distribution and results were correlated with tumor grade, stage, DNA ploidy status (Feulgen spectroscopy) and disease recurrence. PSMA target validation was also performed on a separate group of fresh frozen normal prostate and PCA specimens by transcriptional profiling (TP) using cDNA microarrays, RT-PCR (TaqMan™), in situ hybridization, RT-PCR after laser capture microdissection (LCM), Western Blotting and IHC.

Example 1

Qualitative and Statistical Analysis of Samples from PCA Patients

Specimen Collection, Tumor Grading, and Pathologic Staging

One hundred and thirty-six patients who underwent radical prostatectomy for biopsy proven prostate adenocarcinoma (PAC) between 1987 and 1997 at the Albany Medical Center Hospital were randomly selected: Hematoxylin and eosin stained slides from each radical prostatectomy specimen were reviewed, and a Gleason grade (Gleason (1992) Human Pathol. 23:273-279) and pathologic stage (Ohori et al. (1994) Cancer 74:104-114) were assigned. During review, multiple blocks were identified based on the presence of adequate tumor and the representative nature of the overall tumor grade. Tumors were classified as high grade when the combined Gleason score was 7 or above and as low grade when the combined score was 6 or below. Serum prostate specific antigen (PSA) levels were obtained from the patient's medical records in every case. Serum PSA was measured by the Hybritech® tandem method (Beckman Coulter, Inc., Brea, Calif.). A post-surgical elevation of the PSA level from a baseline level of 0 ng/ml to greater than 0.4 ng/ml on two consecutive occasions was considered as biochemical evidence of disease recurrence. Follow-up information was obtained from review of the patient's medical records.

Immunohistochemistry

Immunohistochemical staining for PSMA was performed by an automated method on the Ventana ES immunohistochemistry instrument (Ventana Medical Systems, Inc., Tucson, Ariz.) utilizing an indirect biotin avidin diaminobenzidine (DAB) detection system on contiguous formalin-fixed paraffin-embedded (FFPE) 4-micron sections from a representative block in each case. Following deparaffinization to water, the antigenic determinant sites were unmasked in Citra with steam for 60 minutes for PSMA detection. The primary antibody, (clone 7E11) mouse anti-human PSMA is an IgG1 class mouse monoclonal directed against the internal domain of the PSMA protein (antibody provided by Millennium Pharmaceuticals, Inc.). The secondary antibody was biotinylated goat anti-mouse immunoglobulins (DAKO Carpenteria, Calif.) at a dilution of 1:250. After the development of the color with DAB, the slides were counterstained with hematoxylin. Benign elements in all cases served as internal positive controls. To confirm the specificity of the primary antibody, negative control slides were run with every batch, an isotype matched immunoglobulin (Sigma, St. Louis, Mo.) at the same concentration as that of the primary antibody.

Staining Interpretation

Immunoreactivity for PSMA was interpreted without prior knowledge of any of the clinicopathologic parameters. The intensity of staining and the distribution of cytoplasmic positivity were considered in the semiquantitative assessment of the immunohistochemical results for both antibodies. The distribution of staining in the tumor cells was graded as focal (≦10%), regional (11-50%) or diffuse (>50%). The intensity of cytoplasmic staining was subjectively graded as weak, moderate or intense. Cases in which the staining patterns were categorized as intense diffuse, intense regional, moderate diffuse, and moderate regional were considered positive for expression of the two proteins. Cases in which the staining patterns were categorized as intense diffuse, intense regional and moderate diffuse were considered as overexpressing PSMA protein.

Quantitative DNA Analysis

Five-micron FFPE sections were stained by the Feulgen method and analyzed for DNA content with the CAS 200 Image Analyzer (Cell Analysis Systems, Lombard, Ill.). After the instrument was calibrated against similarly stained tetraploid rat hepatocytes, the DNA content of the PACs was measured in a minimum of 100 tumor cells and the tumor DNA index was determined by comparison with the control diploid cells of the benign prostatic epithelium. All the tumor cell histograms were reviewed without knowledge of the tumor grade, stage, recurrence status, or immunohistochemical results. A DNA index of 0.77-1.22 was considered to be diploid. Peaks in the tetraploid region containing less than 15% of the total cell population were considered to be the $G_2M$ components of diploid cell populations. Tumors with tetraploid peaks greater than 15% and hyperdiploid, non-tetraploid peaks were considered to be non-diploid (aneuploid) (Smith-Jones et al. (2000) *Cancer Res* 60:5237-5243).

Statistical Analysis

Statistical comparisons were carried out with the STATA software (Stata Corporation, College Station, Tex.). The chi-square test was used to determine the significance of the associations between PSMA expression and pathologic variables. The t test was used to test the equality of the means between overexpressing and non-overexpressing groups. Disease recurrence analysis was performed with univariate models and by the Kaplan-Meier method. Multivariate analysis including clinicopathologic parameters and PSMA expression was performed using the Cox proportional hazards model. The level of significance was set at p<0.05.

PSMA Protein Expression by Immunohistochemistry (IHC)

Figure 1B:
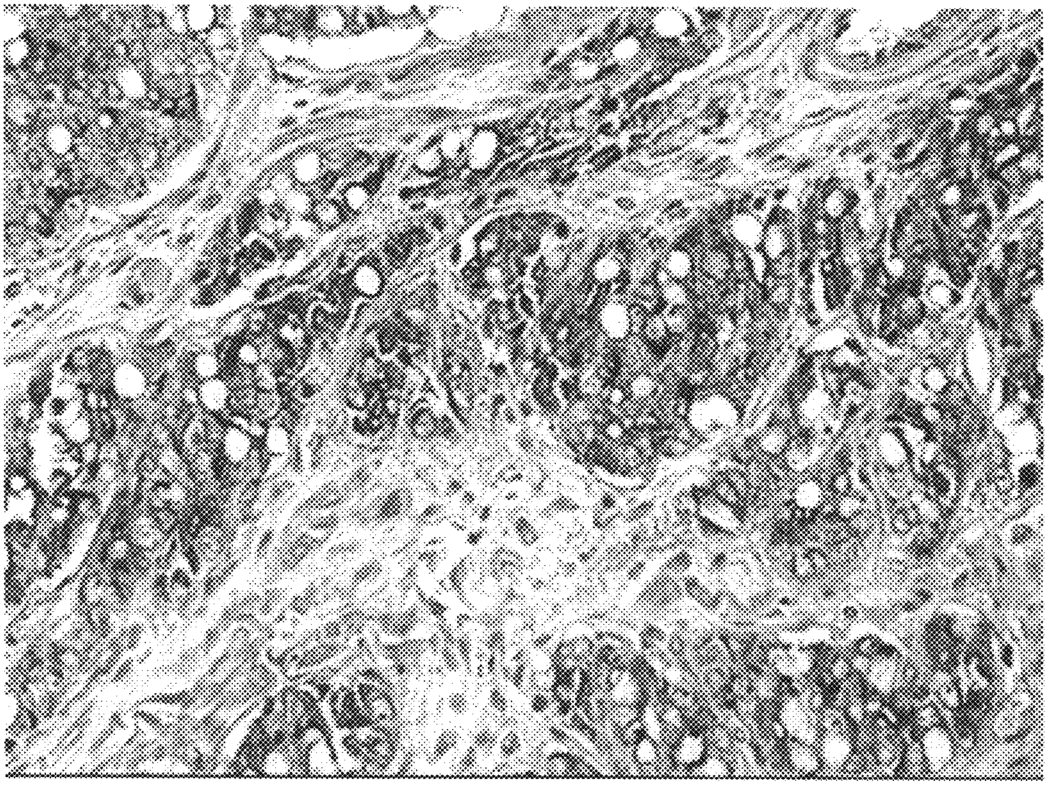
FIG. 1B is a photograph showing significant PSMA overexpression detected by immunohistochemistry in a 61 year old Caucasian man with an organ-confined Stage II Gleason 7 tumor that recurred at 44 months and progressed to hormone refractory metastatic disease (anti-PSMA with 7E11 antibody, peroxidase-antiperoxidase with hematoxylin counterstain X 200).

The specimens used for the paraffin tissue IHC-based clinical outcome study came from 136 patients with a mean age of 66 years (range 49-94) and the mean pre-operative PSA level was 12.4 ng/ml (range 1.6-87.8 ng/ml). Of the 136 PACs, there were 76 (56%) low grade (Gleason score≦6), and 60(44%) high grade (Gleason score>7) tumors. At prostatectomy, there were 83(61%) organ confined tumors (stages I and II) and 53(39%) advanced stage (III and IV) tumors. Of the 96 cases previously analyzed for total DNA content, 68(71%) were diploid and 28(29%) were non-diploid. Follow-up information was available for all patients, of which 52(38%) had biochemical post-surgical disease recurrence. The immunostaining pattern for PSMA was cytoplasmic with tumor cells showing moderate to intense positivity as opposed to relatively weaker expression in benign elements. All prostate cancer cases expressed PSMA (FIG. 1A) at diffuse weak staining or greater. Sixty-five of 136(48%) of the prostate cancers over-expressed PSMA as defined by the presence of focal or diffuse intense staining (FIG. 1B). PSMA overexpression was significantly associated with high tumor grade (p=0.04). The mean Gleason score of tumors with background PSMA expression was 5.92 and the mean Gleason score of the tumors with PSMA overexpression was 6.33. PSMA over-expression was also associated with the presence of non-diploid tumors (p=0.010). The mean DNA index for the PSMA overexpressing tumors was 1.32 compared to a mean DNA index of 1.03 for the tumors with background levels of PSMA expression (p=0.002). PSMA expression status was also associated with advanced tumor stage with 33/57 (58%) Stage III or IV tumors overexpressing PSMA as compared to 31/79 (39%) cases not overexpressing PSMA (p=0.029). The mean serum PSA level of 18.28 ng/ml at the time of diagnosis for the PSMA overexpressing tumors was significantly greater than the mean serum PSA of 9.10 ng/ml for the non-overexpressing group (p=0.006).

TABLE 1

Correlation of PSMA Expression Status with Clinical Parameters and Disease Outcome in 136 Cases of Prostate Cancer Treated by Radical Prostatectomy

| 136 Cases | 71 PSMA (−) | 65 PSMA (+) | Significance |
|---|---|---|---|
| Preoperative PSA | 9.10 +/− 5.91 | 18.28 +/− 17.70 | p = 0.006 |
| Tumor Grade Gleason | 5.92 +/− 1.20 | 6.33 +/− 1.21 | p = 0.04 |
| DNA Index | 1.03 +/− 0.33 | 1.32 +/− 0.50 | p = 0.002 |
| Tumor Stage III/IV (53 Cases) | 31/79 (39%) | 33/57 (58%) | p = 0.029 |
| Recurrent Disease | 20/71 (28%) | 37/65 (57%) | p = 0.001 |
| Time to Recurrence | 43.75 | 34.78 | p = 0.001 |

Figure 2:
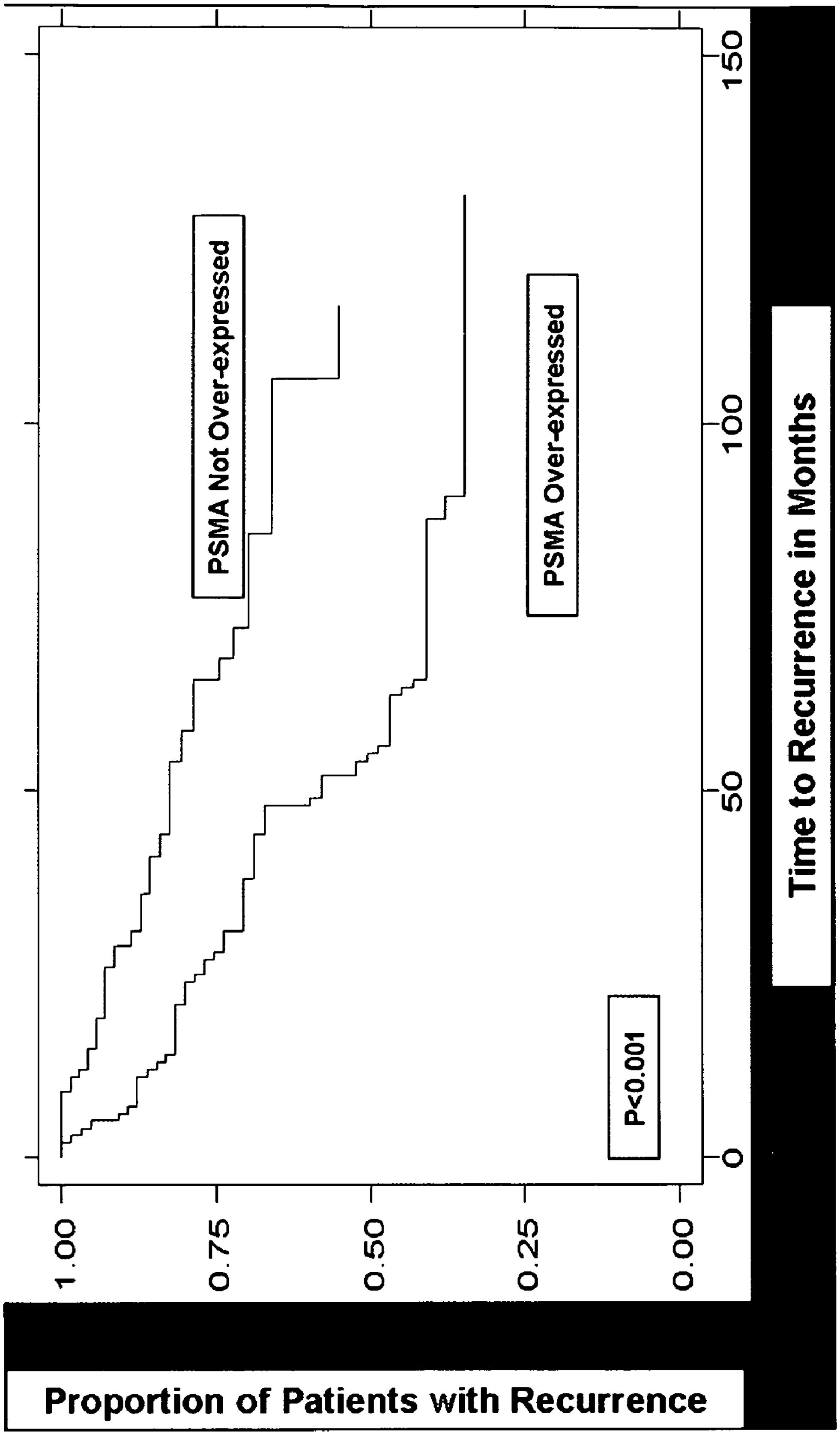
FIG. 2 is a graph showing Kaplan-Meier survival curves for PSMA expression in prostatic adenocarcinomas. Patients with prostatic adenocarcinomas with relatively increased expression of PSMA protein compared to patients whose tumors featured a baseline PSMA expression level suffered a significantly increased rate of recurrent disease (p=0.001).

Univariate Analysis for Disease Relapse. On univariate analysis using available clinical follow-up in all 136 cases, PSMA expression status significantly correlated with biochemical disease recurrence (p=0.001) [FIG. 2].

Multivariate Analysis for Disease Recurrence. On multivariate analysis, advanced tumor stage (p=0.018) and PSMA overexpression (p=0.002) were independent predictors of biochemical recurrence.

In the paraffin-embedded prostatectomies, 100% of the PCAs expressed increased levels of PSMA compared to adjacent benign elements. In the primary tumors, increasing PSMA expression by IHC correlated with tumor grade (p=0.030), stage (p=0.029), aneuploidy (p=0.010), and biochemical recurrence (p=0.001). The mean serum PSA level of 18.28 ng/ml at the time of diagnosis for the PSMA overexpressing tumors was significantly greater than the mean serum PSA of 9.10 ng/ml for the non-overexpressing group (p=0.006). On multivariate analysis, tumor stage (p=0.018) and PSMA expression (p=0.002) were independent predictors of biochemical recurrence.

Western Blotting

Western blot analysis was performed following SDS-polyacrylamide gel electrophoreses of NP-40 tissue extracts and transferred to nylon membranes. The lanes included PSMA in normal/BPH, in situ, and primary adenocarcinoma species of human prostate. Protein extracts from the PSMA and cultured LNCaP prostate tumor cell line were also run as controls. The blots were blocked and incubated with either the anti-PSMA mouse monoclonal antibody 7E11, followed by washing and detection using horseradish peroxidase conjugated goat anti-mouse IgG and chemiluminescent substrate.

Western blot analysis using the 7E11 monoclonal antibody confirmed that neoplastic prostate specimens had higher levels of immunodetectable PSMA protein. In this blot, all prostate clinical tissues were found to have some degree of immunodetectable PSMA protein, but increased levels were clearly evident in a subset of PCAs and the PIN specimen.

Western Blot results supported the IHC findings showing tumor associated upregulation of immunoblottable PSMA in malignant disease that migrated at the appropriate molecular weight.

Example 2

Profiling PSMA Expression

Transcriptional Profiling: Transcriptional profiling was carried out by preparing radioactive probes from total RNA isolated from snap-frozen clinical tissues and hybridizing to nylon membrane microarrays containing DNA from approximately 25,000 human genes. The data was normalized for alu sequences and various housekeeping genes. Expression data was obtained from 25 different specimens of normal prostate and 30 different prostate carcinomas of different stages. For each patient specimen, serum protein values for Prostate Specific Antigen (PSA) were provided as an indicator of disease status.

Figure 3:
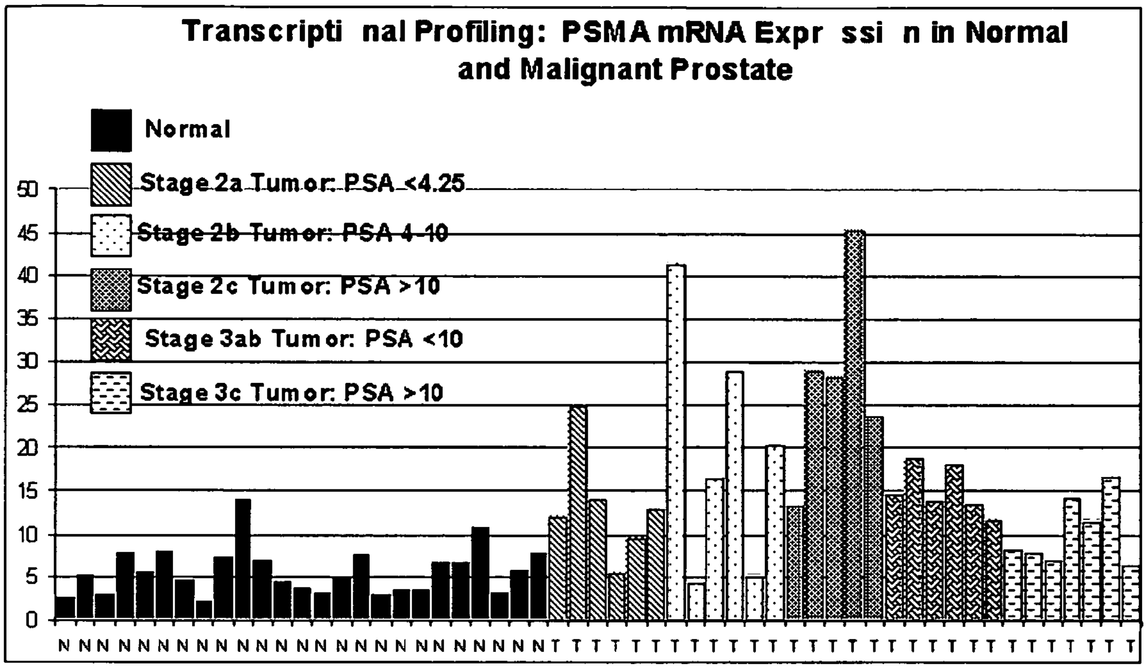
FIG. 3 is a graph showing the relative expression levels of PSMA mRNA obtained upon transcriptional profiling of normal prostate and prostate carcinomas. The tumors were classified by Stage and by the level of serum PSA measured in the patients. The data was normalized for alu sequences and various housekeeping gene. Expression data and PSA serum values were obtained from 25 different specimens of normal prostate and 30 different prostate carcinomas of different stages.

Transcriptional profiling of RNA isolated from 25 normal prostates and 30 PCAs of different stages on 25,000 gene microarrays revealed that PSMA mRNA was prominently expressed in normal prostate with significant elevation in a subset of primary prostate carcinomas (FIG. 3). In this subset of profiled cases, there was no clear cut association between the elevation of prostate tumor PSMA mRNA and baseline PSA serum protein levels. Although, there was considerable variability in PSMA expression between clinical specimens, significant upregulation was clearly evident in a subset of prostate tumors at all Stages of the disease compared to the average levels found in normal tissues.

On TP, PSMA mRNA expression was predominantly limited to normal and malignant prostate with increased levels over normal in a subset of PCAs.

RNA Isolation, cDNA Synthesis, & Real Time RT-PCR

Profiling of PSMA mRNA expression in human tissues was carried out by the real time, reverse transcription, polymerase chain reaction technique using the TaqMan™ system (Applied Biosystems, Inc., Foster City, Calif.). PSMA TaqMAN™ Probe design was based on Accession #M99487 from the NCBI website. This accession number is entitled "Human prostate-specific membrane antigen (PSM) mRNA, complete cds" and is dated Jan. 8, 1995. The sequences were chosen to common domain found in all variants reported for PSMA (PSM—long & PSM'—short. The nucleotide numbers used correspond with the above accession number: (P1) Probe: 5'-tggctcagcaccaccagatagcagc-'3 (spans nucleotides 1191-1215) (SEQ ID NO:3). (F1) Forward primer: 5'-CTATGATGCACAGAAGCTCCTAGAA-3' (SEQ ID NO:4) (R1) Reverse primer: 5'-TGTAGGGCACTTTGAGACTTCCT-3' (SEQ ID NO:5). The quality check of the designed TaqMan™ reagents was performed using a synthetic amplicon and the demonstration of a linear range of 7 logs and a slope of 3.3, which passed the standard curve analysis.

RNA and cDNA were prepared from pathologist verified human clinical specimens and from appropriate cultured cells to establish 3 different cDNA panels with which to evaluate tissue, cell, and disease specific expression of PSMA by TaqMan T analysis. The panels are: 1) Human Cell & Organ Recital Panel; and 2) Human Prostate Tissue Panel. The composition of each of the panels is described in the Results and Discussion sections.

Total RNA was isolated from tissues and cells according to manufacturer's protocol (Tel-Test Incorporation), but with one additional phenol:chloroform extraction. RNA quality was assessed using an Agilent Bioanalyzer 2100 with the RNA 6000 Nano Labchip Kit. Ratios of 28S/18S rRNAs were determined and only specimens with ratios greater than 1 and without notable RNA degradation were acceptable for cDNA preparation. 100 μl of cDNA was generated from 2 ug of DNased RNA using the Reverse Transcriptase Kit (Applied Biosystems) with both random hexamers and oligo d(T) added as primers. All samples had a 'no reverse transcriptase' control set up to assess residual DNA contamination. Samples were subject to the following sequential reverse transcription reaction conditions: 25° C. for 10 minutes, 42° C. for 60 minutes, 95° C. for 5 minutes, and 4° C. holding until quality control analysis. cDNA quality control involved the quantitation of two housekeeping genes (18S and β2-microglobulin) using TaqMan™ on the ABI 7700 instrument with Universal PCR Master Mix and AmpliTaq Gold DNA (Applied Biosystems). Reaction conditions were: initial 50° C. for 2 minutes; hold 95° C. for 10 minutes; and 40 cycles at 95° C. for 15 seconds and 60° C. for 1 minute. Passing criteria for cDNA was as follows: 18S (No Template Control [NTC] Ct value$\geqq$35 and +RT$\leqq$15) and β2-microglobulin (NTC Ct value$\geqq$35 and +RT$\leqq$23). For long term storage, cDNAs were placed at −20° C. and as aliquots if large volumes of cDNAs have been generated.

Tissues used for generating RNA/cDNA and frozen sections for in situ hybridization and laser capture were obtained from public repositories and academic institutions following the various institutional agreements that ensure patient consent and confidentiality: BWH—Brigham and Women's Hospital; CHT—Collaborative Human Tissue Network; CLN—Clinomics, Inc.; JHH—Johns Hopkins Hospital; MPI—Millennium Pharmaceuticals, INC.; NDR—National Disease Research Inc.; PIT—University of Pittsburgh; and TEM —Temple University.

Quality checked tissue and cell cDNAs were then pipetted into 96 well reaction plates. The endogenous control (β2-microglobulin) and PSMA specific primers and probes were added to the cDNAs and TaqMan™ ran and analyzed. The data for each of the panels are presented as bargraphs of the relative expression values derived from the Tabulated TaqMan™ results. Listed under the bargraphs are the mean Ct values obtained for PSMA and the endogenous control housekeeping gene, β2-microglobulin, the normalized and calibrated differences, and the relative expression calculations. These parameters are defined as follows: Ct=a TaqMan™ term that stands for threshold cycle that is the point at which PCR amplification cross the baseline threshold; δCt=a TaqMan™ term that denotes the threshold PCR cycle for a target gene normalized to a housekeeping gene Ct values; δδCt=a TaqMan™ term that represents the calibrated, normalized PCR cycle for a target; and Expression=a TaqMan™ term that denotes the relative expression of target gene obtained by calculating the $2^{-\delta\delta Ct}$ value.

Figure 4:
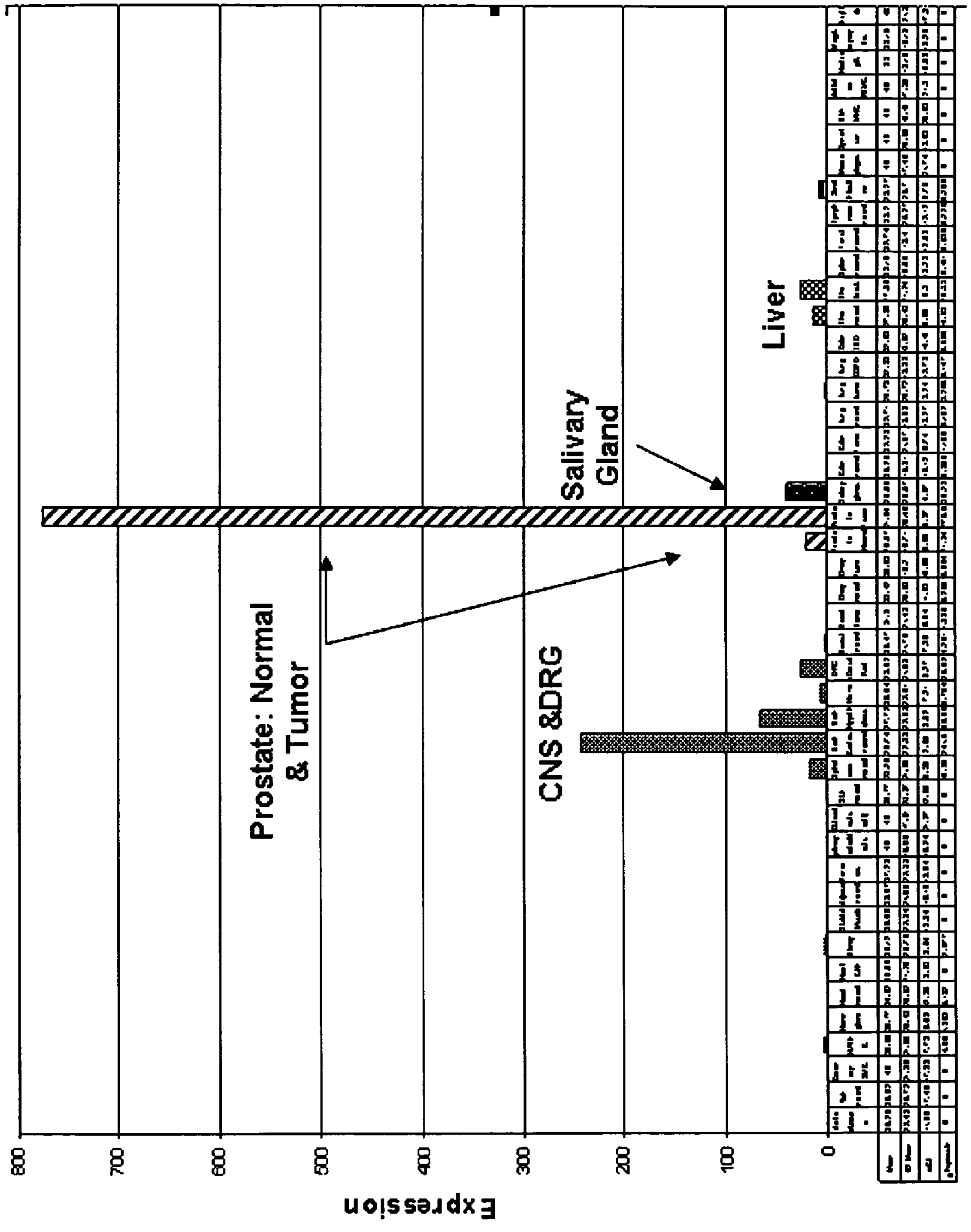
FIG. 4 is a graph showing the tabulated TaqMan™ analysis of PSMA expression in the Human Cell & Organ Recital Panel from Table 2. Data indicates predominant expression of PSMA in prostate tumors followed by the nervous system, salivary gland, normal prostate and liver. The following is a list of the clinical abbreviations used in the panels: ACA=Adenocarcinoma; Arr=arrested; β2=beta 2 microglobulin; BM-MNC=bone marrow derived mononuclear cells; CHF=congestive heart failure; CNS=central nervous system; COPD=chronic obstructive pulmonary disease; DRG=dorsal root ganglion; H=human; HMVECs=human microvascular endothelial cells; HT=hypertensive; HUVEC=human umbilical vein endothelial cells; Hyper=hypertensive; IBD=inflammatory bowel disease; Liv=liver; Met=metastasis; N=Normal; PBMC=peripheral blood mononuclear cells; Prol=proliferative; PSMA=prostate specific membrane antigen; Sm=small; SMC=cultured smooth muscle cells; T=tumor.

A Human Cell & Organ Recital cDNA Panel was created consisting of cDNAs from isolated cell populations, cultured cell lines, and pools of 3 specimens each from a variety of tissues. Specimens in this panel included: diseased aorta, vein, cultured coronary smooth muscle cells, cultured human umbilical vein endothelial cells (HUVECs), hemangioma, heart, diseased heart (congestive heart failure), kidney, skeletal muscle, adipose tissue, pancreas, cultured primary osteoblasts, cultured differentiated osteoclasts, skin, spinal cord, brain cortex, hypothalamus, nerve, dorsal root ganglia, breast, breast tumor, ovary, ovarian tumor, prostate, prostate tumor, salivary gland, colon, colon tumor, lung, lung tumor, chronic obstructive pulmonary diseased lung, inflammatory bowel diseased colon, liver, fibrotic liver, spleen, tonsil, lymph node, small intestine, macrophages, synovium, bone marrow mononuclear cells, activated peripheral blood monocytes, neutrophils, megakaryocytes, erythroid cells and a positive control consisting of pooled cDNAs from RAJI cells, testis, placenta, & brain. This cDNA panel was probed for expression of PSMA using TaqMan™ reagents that detect the expression of both the external domain and cytoplasmic forms of PSMA. Pooled prostate tumor specimens demonstrated the highest PSMA expression with greater than 37 fold relative increases in expression compared to the pooled non-cancerous normal prostate and BPH samples. The next highest expressing non-prostate tissues were found to be in the nervous system with the rank order as: cortex>hypothalamus>dorsal root ganglia>spinal cord>nerve. Other tissues with measurable but low mRNA levels were salivary gland, liver fibrosis, liver, small intestine, HUVECs, lung tumor, breast, kidney and hemangioma. (Table 2 & FIG. 4).

TABLE 2

Human Cell and Organ Recital Panel

| Tissue Type | PSMA Mean Ct | β 2 Mean Ct | ∂∂ Ct | Expression |
|---|---|---|---|---|
| Artery normal | 31.9 | 21.9 | 9.18 | 1.724 |
| Aorta diseased | 35.26 | 22.48 | 11.96 | 0 |
| Vein normal | 39.02 | 20.72 | 17.49 | 0 |
| Coronary SMC | 40 | 21.36 | 17.83 | 0 |
| HUVEC | 30.59 | 21.99 | 7.78 | 4.5497 |
| Hemangioma | 30.77 | 20.43 | 9.53 | 1.3526 |
| Heart normal | 34.62 | 20.92 | 12.89 | 0.1322 |
| Heart CHF | 36.06 | 21.26 | 13.98 | 0 |
| Kidney | 30.12 | 20.76 | 8.54 | 2.6773 |
| Skeletal Muscle | 36.99 | 22.84 | 13.34 | 0 |
| Adipose normal | 38.97 | 21.96 | 16.19 | 0 |
| Pancreas | 37.23 | 22.88 | 13.54 | 0 |
| primary osteoblasts | 40 | 19.95 | 19.24 | 0 |
| Osteoclasts (diff) | 40 | 17.91 | 21.27 | 0 |
| Skin normal | 36.77 | 23.37 | 12.59 | 0 |
| Spinal cord normal | 28.26 | 21.56 | 5.89 | 16.8629 |
| Brain Cortex normal | 25.74 | 22.88 | 2.05 | 241.4841 |
| Brain Hypothalamus normal | 27.72 | 22.98 | 3.92 | 66.0636 |
| Nerve | 30.04 | 22.01 | 7.21 | 6.7542 |
| DRG (Dorsal Root Ganglion) | 28.02 | 21.93 | 5.27 | 25.9162 |
| Breast normal | 30.47 | 21.75 | 7.89 | 4.2011 |
| Breast tumor | 31.8 | 21.43 | 9.54 | 1.3387 |
| Ovary normal | 33.42 | 20.68 | 11.93 | 0.2563 |
| Ovary Tumor | 30.98 | 19.2 | 10.96 | 0.5038 |
| Prostate Normal | 26.07 | 19.71 | 5.55 | 21.3444 |
| Prostate Tumor | 21.64 | 20.46 | 0.37 | 776.4689 |
| Salivary glands | 25.56 | 20.07 | 4.67 | 39.2817 |
| Colon normal | 30.25 | 19.31 | 10.12 | 0.8986 |

TABLE 2-continued

Human Cell and Organ Recital Panel

| Tissue Type | PSMA Mean Ct | β 2 Mean Ct | ∂∂ Ct | Expression |
|---|---|---|---|---|
| Colon tumor | 32.23 | 21.67 | 9.74 | 1.1654 |
| Lung normal | 32.71 | 18.63 | 13.27 | 0.1016 |
| Lung tumor | 29.78 | 20.72 | 8.24 | 3.2962 |
| Lung COPD | 32.38 | 18.83 | 12.73 | 0.1467 |
| Colon IBD | 32.98 | 18.02 | 14.15 | 0.055 |
| Liver normal | 27.39 | 20.48 | 6.09 | 14.6293 |
| Liver fibrosis | 27.36 | 21.24 | 5.3 | 25.3829 |
| Spleen normal | 33.15 | 19.06 | 13.28 | 0.1009 |
| Tonsil normal | 32.74 | 18.4 | 13.53 | 0.0848 |
| Lymph node normal | 33.2 | 20.27 | 12.12 | 0.2247 |
| Small intestine normal | 28.27 | 20.7 | 6.75 | 9.2585 |
| Macrophages | 40 | 17.45 | 21.74 | 0 |
| Synovium | 40 | 20.56 | 18.63 | 0 |
| BM-MNC | 40 | 19.16 | 20.03 | 0 |
| Activated PBMC | 40 | 17.89 | 21.3 | 0 |
| Neutrophils | 38 | 18.16 | 19.03 | 0 |
| Megakaryocytes | 38.19 | 19.13 | 18.25 | 0 |
| Erythroid | 40 | 21.31 | 17.88 | 0 |

Table 2 Legend:

Tabulated TaqMan™ data for the Human Cell & Organ Recital Panel listing the mean Ct values obtained for PSMA and the housekeeping gene, β2-microglobulin, the normalized and calibrated differences, and relative expression calculations.
The various parameters listed are defined as follows:

Ct = a Taqman™ term that stands for threshold cycle that is the point at which PCR amplification cross the baseline threshold;
δCt = a Taqman™ term that denotes the threshold PCR cycle for a target gene normalized to a housekeeping gene Ct values;
δδCt = a Taqman™ term that represents the calibrated, normalized PCR cycle for a target; and
Expression = a Taqman™ term that denotes the relative expression of target gene obtained by calculating the $2^{-\delta\delta Ct}$ value.

Figure 5:
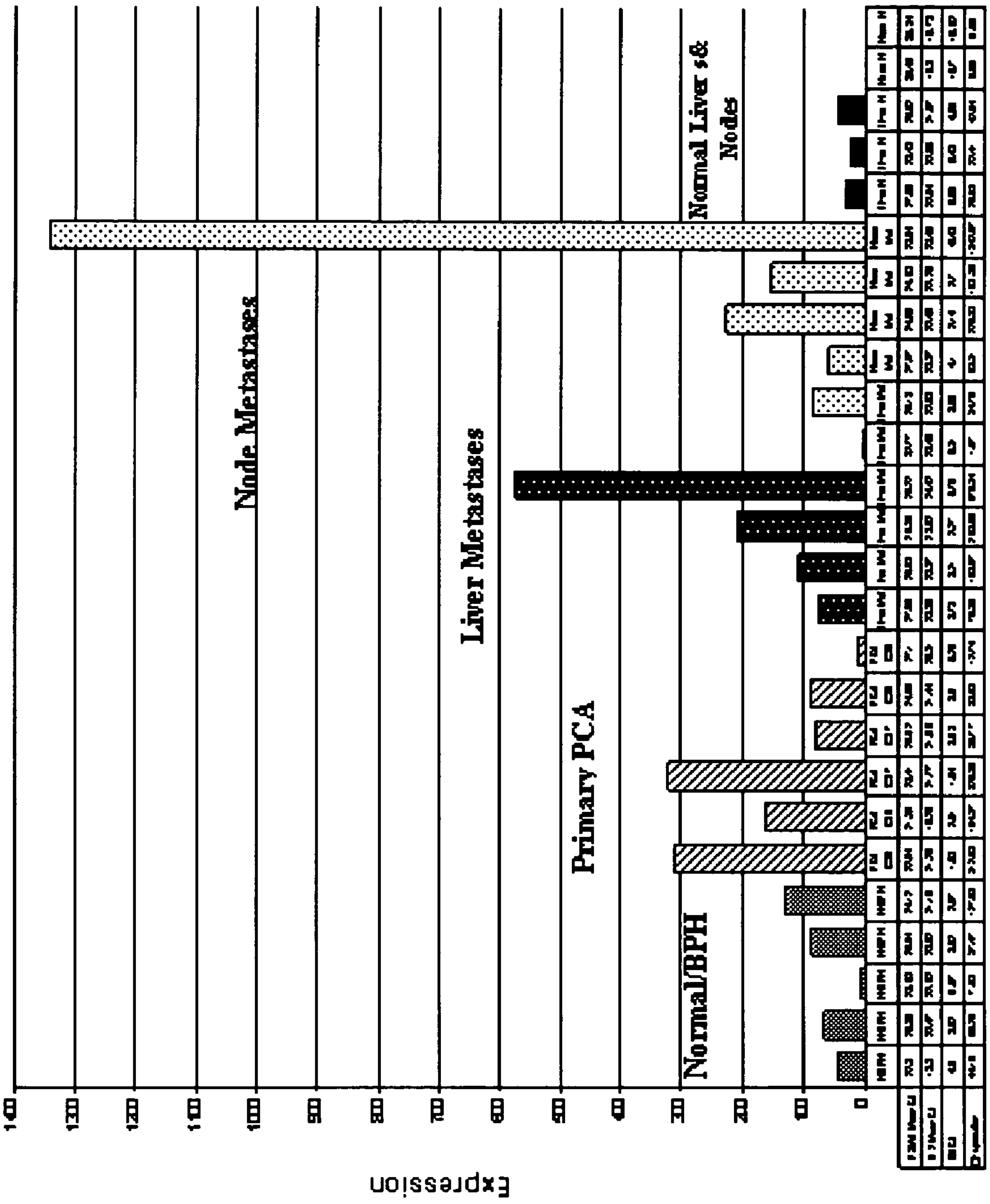
FIG. 5 is a graph showing the TaqMan™ Analysis of PSMA in Prostate Tissue Panel from Table 3. Data shows PSMA mRNA relative expression when normalized to β2-microglobulin in several specimens of normal/BPH prostate, primary tumor, and liver and lymph node metastases, and the normal liver and node control tissues. PSMA transcripts were detected in all prostate specimens with upregulation in a subset of malignancies. No to low PSMA was detected in normal nodes and liver, respectively.

The Human Prostate Tissue cDNA Panel consists of cDNAs derived from: normal prostate and BPH tissues (5 samples), primary prostate tumors (6 samples with Gleason Scores [GS] 5-9), prostate liver metastases (6 samples), prostate lymph node metastases (4 samples), normal liver (3 samples), and normal lymph nodes (2 samples). As shown in FIG. 5 and Table 3, a subset of primary tumors and metastases demonstrated greater expression of PSMA compared with normal prostate and BPH tissues, liver or lymph node. Very low levels and no PSMA transcripts were detected in normal livers and lymph nodes, respectively. For those malignant specimens that exhibited higher expression than the averaged normal/BPH values, the degree of PSMA upregulation was variable ranging from 1.1 to 20 fold. The TaqMan™ RT-PCR quantitation of PSMA mRNA demonstrated the same pattern of expression as observed in the transcriptional experiments with upregulation of PSMA in a subset of tumors, wide variability in overexpression.

TABLE 3

TaqMan™ Analysis of PSMA in Prostate Clinical Specimens

| Tissue Type | PSMA Mean Ct | β 2 Mean Ct | ∂∂ Ct | Expression |
|---|---|---|---|---|
| N/BPH | 22.8 | 18.3 | 4.5 | 44.19 |
| N/BPH | 26.39 | 22.47 | 3.92 | 66.29 |
| N/BPH | 28.98 | 22.02 | 6.97 | 7.98 |
| N/BPH | 26.54 | 23.02 | 3.52 | 87.47 |
| N/BPH | 24.12 | 21.15 | 2.97 | 127.63 |
| PCA: GS5 | 22.94 | 21.26 | 1.68 | 312.08 |
| PCA: GS5 | 21.86 | 19.26 | 2.61 | 164.37 |
| PCA: GS7 | 23.41 | 21.77 | 1.64 | 320.86 |
| PCA: GS7 | 25.62 | 21.99 | 3.63 | 80.77 |
| PCA: GS9 | 24.95 | 21.44 | 3.5 | 88.08 |
| PCA: GS9 | 27.1 | 20.81 | 6.29 | 12.74 |
| Liver Met | 27.59 | 23.86 | 3.73 | 75.36 |
| Liver Met | 26.58 | 23.37 | 3.21 | 108.07 |
| Liver Met | 25.89 | 23.62 | 2.27 | 208.05 |

TABLE 3-continued

TaqMan ™ Analysis of PSMA in Prostate Clinical Specimens

| Tissue Type | PSMA Mean Ct | β 2 Mean Ct | ∂∂ Ct | Expression |
|---|---|---|---|---|
| Liver Met | 25.22 | 24.42 | 0.79 | 576.34 |
| Liver Met | 32.77 | 23.45 | 9.31 | 1.57 |
| Liver Met | 26.18 | 22.63 | 3.56 | 84.79 |
| Node Met | 27.97 | 23.87 | 4.1 | 58.31 |
| Node Met | 24.59 | 22.45 | 2.14 | 226.88 |
| Node Met | 24.98 | 22.29 | 2.7 | 153.89 |
| Node Met | 23.04 | 23.46 | −0.43 | 1342.57 |
| Liver N | 27.09 | 22.04 | 5.06 | 29.98 |
| Liver N | 28.43 | 22.95 | 5.48 | 22.41 |
| Liver N | 26.52 | 21.97 | 4.55 | 42.54 |
| Node N | 36.49 | 19.8 | 16.7 | 0.00 |
| Node N | 36.34 | 19.73 | 16.62 | 0.00 |

Table 3 Legend:

Tabulated TaqMan ™ data for prostate and normal control tissues listing the mean Ct values obtained for PSMA and the housekeeping gene, β2-microglobulin, the normalized and calibrated differences (δCt & δδCt, respectively), and relative expression (the $2^{-\delta\delta Ct}$ value) calculations. The primary tumors have Gleason Scores (GS) indicated.

TaqMan ™ RT-PCR confirmed greater PSMA mRNA expression in a subset of PCAs and metastases. Absent or low PSMA expression was seen in other organs.

Laser Dissection Microscopy with TaqMan™ Analysis of Isolated Cell Populations:

Eight μm sections of frozen normal prostate and prostate carcinoma were separated into epithelial and stromal elements using the Pix Cell™ laser capture microdissection instrument (Arcturus Engineering Inc. Mountain View, Calif.). Typically 1000 to 3000 shots were taken per cap and caps containing isolated cells were used to seal Eppendorf tubes containing 100 uL of RNA isolation reagent. cDNA was prepared and TaqMan™ performed as described above.

Figure 6:
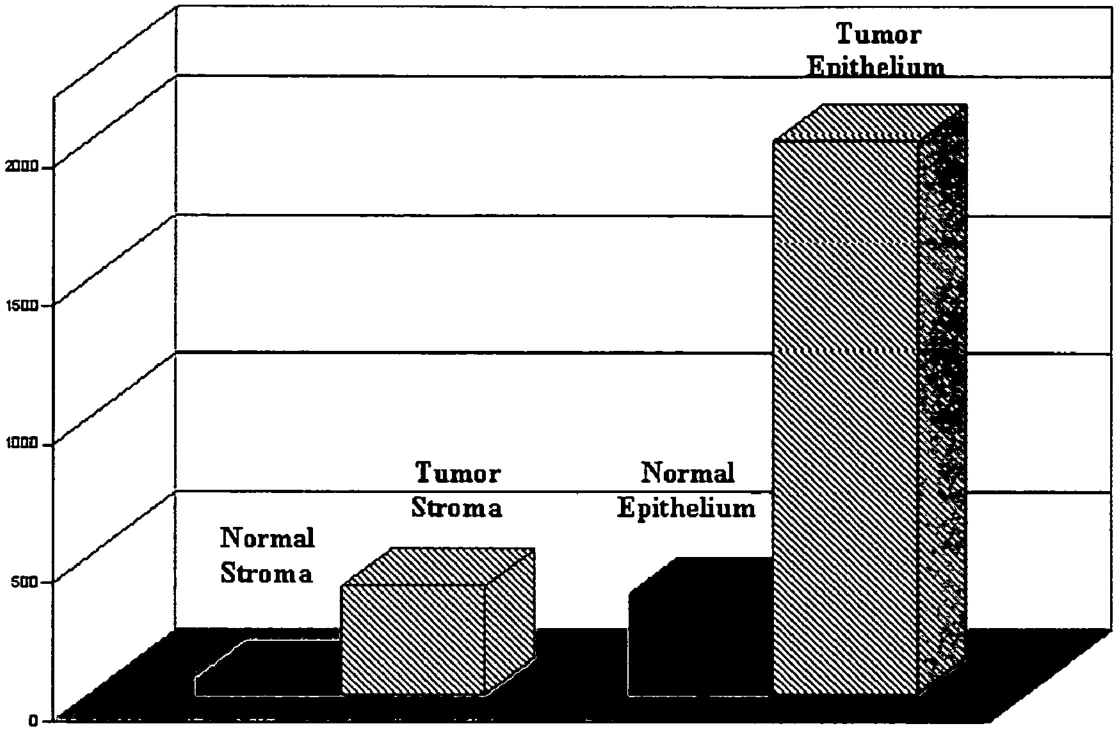
FIG. 6 is a graph showing the TaqMan™ Analysis of PSMA in stroma and epithelium isolated by Laser Captured Microdissection from normal prostate and PCA is shown. Data represents relative expression of PSMA mRNA when normalized to β2-microglobulin.

Laser Capture Microdissection (LCM) enrichment of epithelial and stromal cell populations confirmed that PSMA expression was predominately restricted to the epithelium of the non-cancerous prostate tissues with marked upregulation in the malignant epithelium. (FIG. 6).

LCM enrichment of prostate stroma and epithelium indicated that PSMA mRNA is preferentially expressed in the epithelium and up-regulated with malignant transformation.

In Situ Hybridization

In situ hybridization (ISH) was performed using formalin fixed, acetylated, dehydrated and dilapidated frozen tissue sections with $^{35}S$-labeled riboprobes. Gene specific T3 sense and T7 antisense ISH probes were generated by PCR to domain that is found in all variants of PSMA reported and that spans the TaqMan™ amplification domain. Probes were labeled by reverse transcription (Promega) following the manufacturer's instructions in the presence of $^{35}S$-UTP, unlabeled ATP, GTP, CTP and 200 to 500 ng of DNA template, with purification on MicroSpin G-25 Columns. Slides were hybridized with 50% fomamide, 10 mM Tris-HCL, 0.2 mg/ml yeast tRNA, 1×Denhardt's, 10% Dextran Sulfate, 600 mM NaCl, 0.25% SDS, and $2\times10^6$ cpm/ul of riboprobe. Hybridization was done at 55° C. overnight, followed with washing of slides sequentially at low and high stringency with 2×SSC and 0.2×SCC at 60° C., and then with 20 ug/ml Rnase A, 37° C. The washed hybridized slides were dehydrated, dipped in the NBT2 photographic emulsion (VWR), incubated for 10 to 14 days at 4° C., developed with Kodak Dektol Developer and Fixer, and counterstained with hematoxylin. The results are presented as the range of hybridization intensities estimated by the number of silver grains over the epithelial cells and on the approximate percentage of cells found positive.

Figure 7:
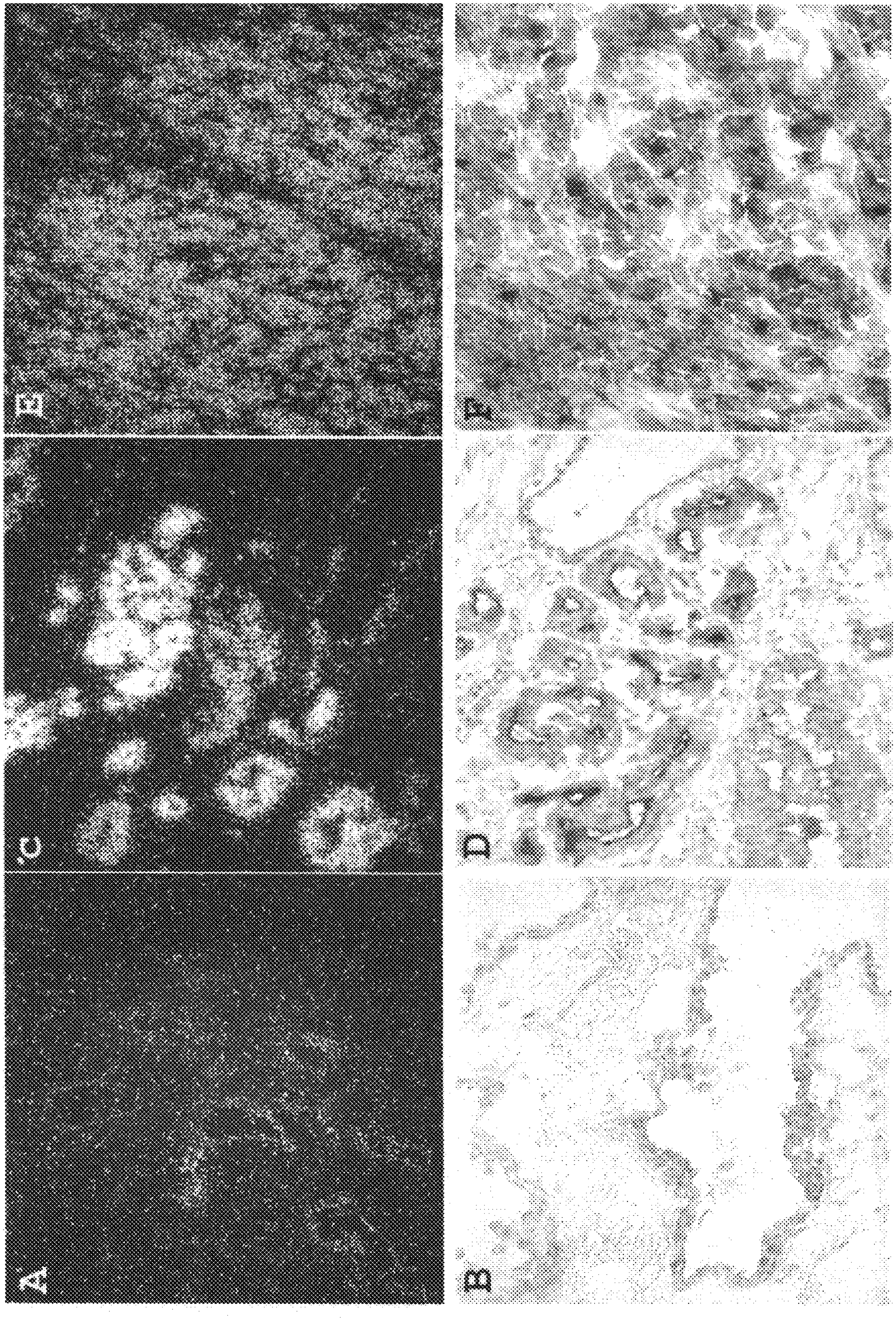
FIG. 7 shows photomicrographs of PSMA mRNA localization by in situ hybridization and of PSMA protein localization by immunohistochemistry in a normal prostate (A & B), a primary prostate adenocarcinoma (C & D), and a lymph node metastasis (E & F).

In situ hybridization was performed on a limited number of frozen sections from normal prostate tissues, PIN (Prostate Intraepithelial Neoplasia), primary prostate cancers and metastatic lesions. PSMA mRNA was preferentially expressed in the epithelium of normal, benign and malignant prostate and correlated with IHC measurements for PSMA protein on the same samples (FIG. 7). There was significant heterogeneity of PSMA mRNA expression, characterized by inter- and intra-gland variability in the signal intensity and in the percentage of positive cells (Table 4). Strong PSMA ISH signal was also a feature of most bone metastases. Liver metastases demonstrated more heterogeneous PSMA mRNA hybridization. Table 5 lists the Gleason Score of tumors subjected to ISH analysis and shows a tendency for higher grade tumors more likely to feature intense areas for PSMA mRNA expression. Six of the primary carcinomas exhibited populations of cells with strong ISH signal for PSMA (2 tumors—GS9, 3 tumors—GS7, and 1 tumor—GS5), 4 tumors exhibited moderate hybridization (1 tumor—GS7, 1 tumor—GS6, and 2 tumors GS5), and 1 GS5 tumor contained no labeled cells.

TABLE 4

PSMA in situ Hybridization Signal in Prostate Tissues.

| | |
|---|---|
| Normal/BPH | 18/19 specimens positive, mostly weak to moderate, with great inter- & intra-gland variability.<br>6/19 [+++] (<50% cells label)<br>12/19 [++ to +] (<75% cells label)<br>1/19 [−] |
| PIN | 5/5 in situ lesions show moderate to strong hybridization<br>3/5 [+++] (>75% cells label)<br>2/5 [++] (<75% cell label) |
| Adenocarcinoma | 10/11 tumors show moderate to strong signal.<br>7/12 [+++] (>50% cells label)<br>3/12 [++ to +] (<75% label)<br>1/12 [−] |
| Lymph Node Mets | 7/8 mets show moderate to high hybridization.<br>7/8 [+++ to ++] (>50% cells label)<br>1/8 [+] (<20% cell label) |
| Liver Mets | 4/7 mets show weak to high signal.<br>3/7 [+++ to +] (>50% cells label)<br>1/7 [++] (<10% cells label)<br>3/7 [−] |
| Bone Mets | 4/5 mets exhibit positive tumor cells having variable intensity signal.<br>2/5 [+++ to +] (>75% cells label)<br>2/5 [++] (<20% cells label)<br>1/5 [−] |

Table 4 Legend:

Summary of in situ hybridization for PSMA mRNA in a panel of normal/BPH prostate, PINs, primary prostate carcinomas, and liver and bone metastases. Hybridization intensity, scored as 3+ to 1+, and the percentage of positive cells are denoted.

TABLE 5

List of Gleason Stage of PCA with their PSMA mRNA hybridization score.

| Gleason Stage | Tissue | Diagnosis | ISH Results Tumor |
|---|---|---|---|
| GS5 | Prostate | Adenocarcinoma/PIN | (+++) |
| GS5 | Prostate | Adenocarcinoma | (−) |
| GS5 | Prostate | Adenocarcinoma | (++) |
| GS5 | Prostate | Adenocarcinoma | (+++) |
| GS6 | Prostate | Adenocarcinoma | (++) |
| GS7 | Prostate | Adenocarcinoma | (++) |
| GS7 | Prostate | Adenocarcinoma | (+++) |
| GS7 | Prostate | Adenocarcinoma | (+++) |
| GS7 | Prostate | Adenocarcinoma | (+++) |
| GS9 | Prostate | Adenocarcinoma | (+++) |
| GS9 | Prostate | Adenocarcinoma | (+++) |

Highest Signal

TABLE 5-continued

| List of Gleason Stage of PCA with their PSMA mRNA hybridization score. | | | |
|---|---|---|---|
| Intensity | GS9 | GS7 | GS5 & GS6 |
| (+++) | 2 tumors | 3 tumors | 1 tumor |
| (++) | | 1 tumor | 3 tumors |
| (−) | | | 1 tumor |

Table 5 Legend:
Association of Gleason Score with PSMA mRNA in situ hybridization intensity. Hybridization intensity, scored as 3+ to 1+, and the percentage of positive cells are denoted.

In situ hybridization demonstrated increased epithelial specific expression of PSMA mRNA in primary PCAs and metastases.

These results suggest that PSMA expression is highly restricted to normal prostate and PCA tissues and, for the first time, that over-expression of immunoreactive PSMA protein in primary tumors independently predicts biochemical disease recurrence. The validation of PSMA as a target of therapy in PCA has recently been accompanied by early results of clinical trials using the radioconjugated anti-PSMA antibody, huJ591, appear to demonstrate significant reductions in serum PSA levels and soft tissue tumor mass shrinkage.

One finding was that overexpression of PSMA protein determined by immunohistochemistry on prostatectomy specimens significantly correlated with higher pre-operative serum PSA levels, high tumor grade, non-diploid DNA content and advanced tumor stage and independently predicted biochemical disease relapse. This appears to be the first attempt to link PSMA levels measured on primary prostatectomy specimens with prostate cancer outcome although increased PSMA expression has been associated with higher tumor grade and metastatic disease. In comparison with the other candidate prognostic factors described above, the detection of PSMA levels in the primary tumor has the advantage of being linked to the specific selection of an anti-PSMA targeted therapy. In the present study the 7E11 anti-PSMA antibody was used for paraffin-based IHC. This antibody was the first PSMA antibody developed and recognizes the internal domain of the PSMA molecule. Subsequently, a series of antibodies were developed that bound to the external domain of the PSMA molecule. The rationale for the development of external domain recognizing antibodies to PSMA were in the anticipation of targeted therapy for prostate cancer and the conjugation of the targeting antibody with radioisotopes, toxins and chemotherapy.

The 7E11 antibody has been used to develop a radioconjugate for diagnostic imaging. $^{111}$In Capromab Pendetide (Prosta-Scint$^{R}$) immunoscintigraphy has been used for the management of prostate cancer, but has been limited by the dependency of the 7E11 antibody on the exposure of the internal domain of PSMA that will not take place in tumor cells devoid of apoptosis or necrosis. Antibodies to the external domain of PSMA such as the J-591 antibody have recently been introduced for the treatment of HRPC and also show promise as imaging reagents.

An assessment of the regulation of PSMA mRNA expression was also carried out using cDNA microarray transcriptional profiling of over 50 clinical specimens, TaqMan™ real-time RT-PCR quantitation, and in situ hybridization. PSMA mRNA was found to be expressed in all normal and malignant prostate specimens with significant upregulation in a subset of primary tumors and metastases. LCM and in situ studies confirmed that PSMA was preferentially expressed by the prostate epithelium versus the stroma, and often upregulated in malignant cells. These findings are supported by a recent transcriptional profiling study that found that increased PSMA mRNA expression was second only to hepsin-like protease in its association with high grade prostate cancer. Overall, not only do these various molecular techniques demonstrate that PSMA is present in most. if not all, prostate specimens and is increased at the RNA and protein levels in a subset of PCAs and metastatic lesions, but also, these data serve to further validate PSMA as a therapeutic target that may benefit a significant number of prostate cancer patients.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A method of determining if a subject is at risk for prostate cancer recurrence, the method comprising:

providing a sample from a primary tumor of a subject upon diagnosis of prostate cancer; and determining human prostate specific membrane antigen (PSMA) protein levels in the sample, wherein the human PSMA comprises the amino acid sequence of SEQ ID NO:1 and wherein a statistically significant increase in PSMA protein levels relative to a reference standard of PSMA protein levels in a primary tumor of subjects diagnosed with prostate cancer that do not have recurrence indicates a risk of prostate cancer recurrence, thereby determining if the subject is at risk of prostate cancer recurrence.

2. The method of claim 1, wherein the sample is a biopsy sample.

3. The method of claim 1, wherein the sample is obtained from a partial or radical prostatectomy of the subject.

4. The method of claim 1, wherein the risk of recurrence is determined upon diagnosis of prostate cancer.

5. The method of claim 1, wherein the risk of recurrence is determined after the subject is diagnosed with prostate cancer.

6. The method of claim 1, wherein the risk of recurrence is determined after the subject has been treated with an anti-cancer treatment.

7. The method of claim 6, wherein the anti-cancer treatment is a radical or partial prostatectomy.

8. The method of claim 1, wherein PSMA protein levels are determined by a method selected from the group consisting of an enzyme-linked immunosorbent assay (ELISA), a radioimmunoassay (RIA), a Western blot, or an immunohistochemical assay (IHC).

9. The method of claim 1, wherein a subject that does not have a statistically significant increase of PSMA protein levels as compared to the reference standard is assigned a value of 40% or less risk of recurrence.

10. The method of claim 1, wherein a subject that does not have a statistically significant increase of PSMA protein levels as compared to the reference standard is assigned a value of 30% or less risk of recurrence.

* * * * *

```
                          SEQUENCE LISTING

<160> NUMBER OF SEQ ID NOS: 5

<210> SEQ ID NO 1
<211> LENGTH: 750
<212> TYPE: PRT
<213> ORGANISM: Homo sapiens

<400> SEQUENCE: 1

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60
```

-continued

```
Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480
```

-continued

```
Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Ser Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750


<210> SEQ ID NO 2
<211> LENGTH: 693
<212> TYPE: PRT
<213> ORGANISM: Homo sapiens

<400> SEQUENCE: 2

Met Lys Ala Phe Leu Asp Glu Leu Lys Ala Glu Asn Ile Lys Lys Phe
1               5                   10                  15

Leu Tyr Asn Phe Thr Gln Ile Pro His Leu Ala Gly Thr Glu Gln Asn
            20                  25                  30

Phe Gln Leu Ala Lys Gln Ile Gln Ser Gln Trp Lys Glu Phe Gly Leu
        35                  40                  45

Asp Ser Val Glu Leu Ala His Tyr Asp Val Leu Leu Ser Tyr Pro Asn
    50                  55                  60

Lys Thr His Pro Asn Tyr Ile Ser Ile Ile Asn Glu Asp Gly Asn Glu
65                  70                  75                  80

Ile Phe Asn Thr Ser Leu Phe Glu Pro Pro Pro Pro Gly Tyr Glu Asn
                85                  90                  95

Val Ser Asp Ile Val Pro Pro Phe Ser Ala Phe Ser Pro Gln Gly Met
            100                 105                 110
```

-continued

```
Pro Glu Gly Asp Leu Val Tyr Val Asn Tyr Ala Arg Thr Glu Asp Phe
        115                 120                 125

Phe Lys Leu Glu Arg Asp Met Lys Ile Asn Cys Ser Gly Lys Ile Val
    130                 135                 140

Ile Ala Arg Tyr Gly Lys Val Phe Arg Gly Asn Lys Val Lys Asn Ala
145                 150                 155                 160

Gln Leu Ala Gly Ala Lys Gly Val Ile Leu Tyr Ser Asp Pro Ala Asp
                165                 170                 175

Tyr Phe Ala Pro Gly Val Lys Ser Tyr Pro Asp Gly Trp Asn Leu Pro
            180                 185                 190

Gly Gly Gly Val Gln Arg Gly Asn Ile Leu Asn Leu Asn Gly Ala Gly
        195                 200                 205

Asp Pro Leu Thr Pro Gly Tyr Pro Ala Asn Glu Tyr Ala Tyr Arg Arg
    210                 215                 220

Gly Ile Ala Glu Ala Val Gly Leu Pro Ser Ile Pro Val His Pro Ile
225                 230                 235                 240

Gly Tyr Tyr Asp Ala Gln Lys Leu Leu Glu Lys Met Gly Gly Ser Ala
                245                 250                 255

Pro Pro Asp Ser Ser Trp Arg Gly Ser Leu Lys Val Pro Tyr Asn Val
            260                 265                 270

Gly Pro Gly Phe Thr Gly Asn Phe Ser Thr Gln Lys Val Lys Met His
        275                 280                 285

Ile His Ser Thr Asn Glu Val Thr Arg Ile Tyr Asn Val Ile Gly Thr
    290                 295                 300

Leu Arg Gly Ala Val Glu Pro Asp Arg Tyr Val Ile Leu Gly Gly His
305                 310                 315                 320

Arg Asp Ser Trp Val Phe Gly Gly Ile Asp Pro Gln Ser Gly Ala Ala
                325                 330                 335

Val Val His Glu Ile Val Arg Ser Phe Gly Thr Leu Lys Lys Glu Gly
            340                 345                 350

Trp Arg Pro Arg Arg Thr Ile Leu Phe Ala Ser Trp Asp Ala Glu Glu
        355                 360                 365

Phe Gly Leu Leu Gly Ser Thr Glu Trp Ala Glu Glu Asn Ser Arg Leu
    370                 375                 380

Leu Gln Glu Arg Gly Val Ala Tyr Ile Asn Ala Asp Ser Ser Ile Glu
385                 390                 395                 400

Gly Asn Tyr Thr Leu Arg Val Asp Cys Thr Pro Leu Met Tyr Ser Leu
                405                 410                 415

Val His Asn Leu Thr Lys Glu Leu Lys Ser Pro Asp Glu Gly Phe Glu
            420                 425                 430

Gly Lys Ser Leu Tyr Glu Ser Trp Thr Lys Lys Ser Pro Ser Pro Glu
        435                 440                 445

Phe Ser Gly Met Pro Arg Ile Ser Lys Leu Gly Ser Gly Asn Asp Phe
    450                 455                 460

Glu Val Phe Phe Gln Arg Leu Gly Ile Ala Ser Gly Arg Ala Arg Tyr
465                 470                 475                 480

Thr Lys Asn Trp Glu Thr Asn Lys Phe Ser Gly Tyr Pro Leu Tyr His
                485                 490                 495

Ser Val Tyr Glu Thr Tyr Glu Leu Val Glu Lys Phe Tyr Asp Pro Met
            500                 505                 510

Phe Lys Tyr His Leu Thr Val Ala Gln Val Arg Gly Gly Met Val Phe
        515                 520                 525
```

-continued

```
Glu Leu Ala Asn Ser Ile Val Leu Pro Phe Asp Cys Arg Asp Tyr Ala
    530                 535                 540

Val Val Leu Arg Ser Tyr Ala Asp Lys Ile Tyr Ser Ile Ser Met Lys
545                 550                 555                 560

His Pro Gln Glu Met Lys Thr Tyr Ser Val Ser Phe Asp Ser Leu Phe
                565                 570                 575

Ser Ala Val Lys Asn Phe Thr Glu Ile Ala Ser Lys Phe Ser Glu Arg
            580                 585                 590

Leu Gln Asp Phe Asp Lys Ser Asn Pro Ile Val Leu Arg Met Met Asn
        595                 600                 605

Asp Gln Leu Met Phe Leu Glu Arg Ala Phe Ile Asp Pro Leu Gly Leu
    610                 615                 620

Pro Asp Arg Pro Phe Tyr Arg His Val Ile Tyr Ala Pro Ser Ser His
625                 630                 635                 640

Asn Lys Tyr Ala Gly Glu Ser Phe Pro Gly Ile Tyr Asp Ala Leu Phe
                645                 650                 655

Asp Ile Glu Ser Lys Val Asp Pro Ser Lys Ala Trp Gly Glu Val Lys
            660                 665                 670

Arg Gln Ile Tyr Val Ala Ala Phe Thr Val Gln Ala Ala Ala Glu Thr
        675                 680                 685

Leu Ser Glu Val Ala
    690


<210> SEQ ID NO 3
<211> LENGTH: 25
<212> TYPE: DNA
<213> ORGANISM: Homo sapiens

<400> SEQUENCE: 3

tggctcagca ccaccagata gcagc                                           25


<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

ctatgatgca cagaagctcc tagaa                                           25


<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

tgtagggcac tttgagactt cct                                             23
```